US010036026B2

(12) United States Patent
Reed

(10) Patent No.: US 10,036,026 B2
(45) Date of Patent: *Jul. 31, 2018

(54) METHODS FOR DYNAMIC VECTOR ASSEMBLY OF DNA CLONING VECTOR PLASMIDS

(71) Applicant: Intrexon Corporation, Blacksburg, VA (US)

(72) Inventor: Thomas D. Reed, Arlington, VA (US)

(73) Assignee: Intrexon Corporation, Blacksburg, VA (US)

( * ) Notice: Subject to any disclaimer, the term of this patent is extended or adjusted under 35 U.S.C. 154(b) by 419 days.

This patent is subject to a terminal disclaimer.

(21) Appl. No.: 14/825,195

(22) Filed: Aug. 13, 2015

(65) Prior Publication Data

US 2018/0023089 A1 Jan. 25, 2018

Related U.S. Application Data

(63) Continuation of application No. 14/532,088, filed on Nov. 4, 2014, now Pat. No. 9,115,361, which is a continuation of application No. 11/569,335, filed as application No. PCT/US2005/017272 on May 18, 2005, now abandoned.

(60) Provisional application No. 60/572,011, filed on May 18, 2004.

(51) Int. Cl.
| C12N 15/64 | (2006.01) |
| C12N 15/66 | (2006.01) |
| C12N 15/85 | (2006.01) |
| C07H 21/04 | (2006.01) |

(52) U.S. Cl.
CPC ............. *C12N 15/64* (2013.01); *C07H 21/04* (2013.01); *C12N 15/66* (2013.01); *C12N 15/85* (2013.01)

(58) Field of Classification Search
None
See application file for complete search history.

(56) References Cited

U.S. PATENT DOCUMENTS

| 4,661,454 A | 4/1987 | Botstein et al. |
| 4,820,642 A | 4/1989 | Edman et al. |
| 5,061,628 A | 10/1991 | Roberts et al. |
| 5,192,676 A | 3/1993 | Morgan et al. |
| 5,736,135 A | 4/1998 | Goeddel et al. |
| 5,919,667 A | 7/1999 | Gage et al. |
| 6,096,523 A | 8/2000 | Parrott et al. |
| 6,245,545 B1 | 6/2001 | Kong et al. |
| 6,248,569 B1 | 6/2001 | Dunn et al. |
| 6,514,737 B1 | 2/2003 | Zhu |
| 6,720,140 B1 | 4/2004 | Hartley et al. |
| 7,785,871 B2 | 8/2010 | Reed |
| 9,115,361 B2 | 8/2015 | Reed |
| 2002/0146733 A1 | 10/2002 | Sykes et al. |
| 2004/0185556 A1 | 9/2004 | Reed |
| 2004/0253732 A1 | 12/2004 | Lapize-Gauthey et al. |
| 2005/0074883 A1 | 4/2005 | Slater et al. |
| 2005/0090010 A1 | 4/2005 | Hayashizaki et al. |
| 2005/0176099 A1 | 8/2005 | Saha |
| 2008/0050808 A1 | 2/2008 | Reed et al. |
| 2008/0085553 A1 | 4/2008 | Reed et al. |
| 2008/0241915 A1 | 10/2008 | Reed |
| 2009/0123973 A1 | 5/2009 | Reed |
| 2009/0226976 A1 | 9/2009 | Reed |

FOREIGN PATENT DOCUMENTS

| GB | 2 393 441 A | 3/2004 |
| JP | 3-058794 | 3/1991 |
| JP | 10-113186 A | 5/1998 |
| JP | 2000-41680 | 2/2000 |
| JP | 2001-503252 | 3/2001 |
| JP | 2002-360261 | 12/2002 |
| WO | WO 95/18858 A1 | 7/1995 |
| WO | WO 99/21977 A1 | 5/1999 |
| WO | WO 01/07633 A1 | 2/2001 |
| WO | WO 2005/040336 A2 | 5/2005 |
| WO | WO 2005/116231 A1 | 12/2005 |
| WO | WO 2007/038276 A2 | 4/2007 |

OTHER PUBLICATIONS

Whittaker, K.L. et al., "Different 3' untranslated regions target alternatively processed *hu-li tai shao* (hts) transcripts to distinct cytoplasmic locations during *Drosophila oogenesis*," Journal of Cell Science 112: 3385-3398, the Company of Biologists Limited (1999).
English language abstract for Japanese patent publication No. 10-113186, "Gene Coding Thrombopoietin," inventors Dan L. Eaton et al., assignee Genentech, Inc., published May 6, 1998, abstract downloaded on Jan. 7, 2013 from worldwide.espacenet.com.
Mizuguchi, H. and M.A. Kay, "Efficient Construction of a Recombinant Adenovirus Vector by an Improved In Vitro Ligation Method," Human Gene Therapy 9: 2577-2583, Mary Ann Liebert, Inc., New Rochelle, N. Y., U.S.A. (1998).
Office Action dated Oct. 23, 2009 in U.S. Appl. No. 10/682,764, inventor Reed, T., filed Oct. 9, 2003.
Office Action dated Jul. 21, 2010 in U.S. Appl. No. 11/840,297, inventor Thomas D. Reed, filed Aug. 17, 2007.
Office Action dated Jul. 20, 2010 in U.S. Appl. No. 12/090,463, inventor Thomas D. Reed, filed Nov. 12, 2008.
Office Action dated Sep. 1, 2010 in U.S. Appl. No. 11/841,380, inventor Thomas D. Reed, filed Aug. 20, 2007.
Office Action dated Jul. 6, 2010 in U.S Appl. No. 11/840,744, inventor Reed et al, filed Aug. 17, 2007.
Supplementary European Search Report in European Application No. 05751019, dated Sep. 3, 2009 (4 pages).

(Continued)

*Primary Examiner* — James S Ketter
(74) *Attorney, Agent, or Firm* — Sterne, Kessler, Goldstein & Fox P.L.L.C.

(57) ABSTRACT

A method for using cloning vector plasmids to produce DNA molecules, such as transgenes, in a single cloning step. The transgenes can be used for the purpose of gene expression or analysis of gene expression. The plasmid cloning vectors are engineered to minimize the amount of manipulation of DNA fragment components by the end user of the vectors and the methods for their use. Transgenes produced using the invention may be used in a single organism, or in a variety of organisms including bacteria, yeast, mice, and other eukaryotes with little or no further modification.

33 Claims, 2 Drawing Sheets

(56) References Cited

OTHER PUBLICATIONS

International Search Report for International Application No. PCT/US05/17272, International Search Authority/US, Alexandria, VA, U.S.A., dated Oct. 7, 2005 (2 pages).

International Preliminary Report on Patentability for International Application No. PCT/US05/17272 by the International Bureau of WIPO, Geneva, Switzerland, dated Nov. 21, 2006 (7 pages) (Including the Written Opinion of the International Search Authority dated Oct. 7, 2005).

Notice of Allowance dated Mar. 2, 2010 in U.S. Appl. No. 10/682,764, Reed, T., filed Oct. 9, 2003.

Office Action dated Feb. 19, 2010 in U.S. Appl. No. 11/841,380, inventor Reed, T., filed Aug. 20, 2007.

English language abstract for Japanese patent publication No. 2000-41680, "Heat-Resistant Glutamate Dehydrogenase and Its Production," inventors Terajima Chikako et al., assignee Oriental Yeast Co. Ltd., published Feb. 15, 2000, abstract downloaded on Aug. 11, 2011 from worldwide.espacenet.com.

English language abstract for Japanese patent publication No. 3-058794, "Production of Heterogeneic Product by Yeast," inventors Ogi Kazuko et al., assignee Suntory Ltd., published Mar. 13, 1991, abstract downloaded on Aug. 11, 2011 from worldwide.espacenet.com.

English language abstract for WO 98/12207, International Application No. PCT/US97/16639, "High Level Expression of Proteins," inventors Brian Seed et al., assignee General Hospital Corp., published Mar. 13, 2001, abstract downloaded on Aug. 11, 2011 from worldwide.espacenet.com.

English language abstract for Japanese patent publication No. 2002-360261, "DNA Polymerase-Related Factor," inventors Kitabayashi Masao et al., assignee Toyo Boseki, published Dec. 17, 2002, abstract downloaded on Aug. 11, 2011 from worldwide.espacenet.com.

Bray, P.F., et al., "Physical linkage of the genes for platelet membrane glycoproteins IIb and IIIa," *Proc. Natl. Acad. Sci.* 85:8683-8687, National Academy of Sciences (1988).

Jayaraj et al., "GeMS: an advanced software package for designing synthetic genes," *Nucleic Acids Research* 33:3011-3016, Oxford University Press, doi: 10.1093/nar/gki614 (May 23, 2005).

La Fontaine et al., "Eukaryotic Expression Vectors That Replicate to Low Copy Number in Bacteria: Transient Expression of the Menkes Protein," *Plasmid* 39: 245-251, Academic Press (1998).

Lu et al., "Vector NTI, a balanced all-in-one sequence analysis suite," *Briefings in Bioinformatics* 5: 378-388, Henry Stewart Publications (Dec. 2004).

Zabarovska, V., "*Not*I passporting to identify a species composition of complex microbial systems," *Nucl. Acid Res.* 31:E5, Oxford University Press, DOI: 10.1093/nar/gng005, 10 pages (2003).

Office Action dated Apr. 6, 2006 in U.S. Appl. No. 10/682,764, Reed, T., filed Oct. 9, 2003.

Office Action dated Jul. 13, 2007 in U.S. Appl. No. 10/682,764, Reed, T., filed Oct. 9, 2003.

Office Action dated Dec. 5, 2007 in U.S. Appl. No. 10/682,764, Reed, T., filed Oct. 9, 2003.

Office Action dated Oct. 30, 2008 in U.S. Appl. No. 11/233,246, Reed, T., filed Sep. 22, 2005.

U.S. Appl. No. 11/841,380, inventor Reed, T., filed Aug. 20, 2007.

U.S. Appl. No. 10/682,764, inventor Reed, T., filed May 18, 2005, published on Sep. 23, 2004 as U.S. Patent Publication 2004/0185556 A1.

U.S. Application No. 11/233,246, inventors Reed. T., and Zhou, J.F., filed Sep. 22, 2005, published on Feb. 28, 2008 as U.S. Patent Publication 2008/0050808 A1.

U.S. Appl. No. 11/840,744, inventors Reed, T., and Zhou, J.F., filed Aug. 17, 2007, published on Apr. 10, 2008 as U.S. Patent Publication 2008/0085553 A1.

U.S. Appl. No. 11/840,297, inventor Reed, T., filed Aug. 17, 2007, published on Oct. 2, 2008 as U.S. Patent Publication 2008/0241915 A1.

Svoboda, M. et al., "A cDNA construct allowing the expression of rat hepatic glucagon receptors," *Biochemical and Biophysical Research Communications* 192: 135-142, Elsevier, Inc., Philadelphia, P.A. (1993).

Office Action dated Mar. 19, 2009 in U.S. Appl. No. 10/682,764, Reed, T., filed Oct. 9, 2003.

Office Action dated Jul. 10, 2009 in U.S. Appl. No. 11/233,246, Reed, T., filed Sep. 22, 2005.

Two pages from the New England BioLabs Online Catalog, http://web.archive.org/web/20020408135531/www.neb.com/neb/frame_cat.htm, printed on Jun. 22, 2009.

U.S. Appl. No. 11/841,380, inventor Reed, T., filed Aug. 20, 2007, published as US 2009/0226976 A1.

U.S. Appl. No. 12/090,463, inventor Reed, Thomas D. (U.S. National Phase of International Application No. PCT/US2006/060065, filed Oct. 19, 2006), published as US 2009/0123973 A1.

U.S. Appl. No. 11/233,246, inventors Reed, T., and Zhou, J.F., filed Sep. 22, 2005, published on Feb. 28, 2008 as U.S. Patent Publication 2008/0050808 A1.

SEQUENCE LISTING

<160> NUMBER OF SEQ ID NOS: 16

<210> SEQ ID NO 1
<211> LENGTH: 6
<212> TYPE: DNA
<213> ORGANISM: Artificial Sequence
<220> FEATURE:
<223> OTHER INFORMATION: Synthetic EcoR1 endonuclease cleave site

<400> SEQUENCE: 1 gaattc                                                                    6

<210> SEQ ID NO 2
<211> LENGTH: 6

```
<212> TYPE: DNA
<213> ORGANISM: Artificial Sequence
<220> FEATURE:
<223> OTHER INFORMATION: Synthetic EcoR1 endonuclease cleave site

<400> SEQUENCE: 2 cttaag                                                                  6

<210> SEQ ID NO 3
<211> LENGTH: 18
<212> TYPE: DNA
<213> ORGANISM: Artificial Sequence
<220> FEATURE:
<223> OTHER INFORMATION: Synthetic I-ScelI endonuclease cleave site

<400> SEQUENCE: 3
tagggataac agggtaat                                                    18

<210> SEQ ID NO 4
<211> LENGTH: 17
<212> TYPE: DNA
<213> ORGANISM: Artificial Sequence
<220> FEATURE:
<223> OTHER INFORMATION: Synthetic I-ScelI endonuclease cleave site

<400> SEQUENCE: 4
atccctattg tccatta                                                     17

<210> SEQ ID NO 5
<211> LENGTH: 12
<212> TYPE: DNA
<213> ORGANISM: Artificial Sequence
<220> FEATURE:
<223> OTHER INFORMATION: Synthetic BstX I endonuclease cleave site
<220> FEATURE:
<221> NAME/KEY: misc_feature
<222> LOCATION: (4)..(9)
<223> OTHER INFORMATION: n can be nucleotide 'a', 't', 'g', or 'c'

<400> SEQUENCE: 5
ccannnnnnt gg                                                          12

<210> SEQ ID NO 6
<211> LENGTH: 6
<212> TYPE: DNA
<213> ORGANISM: Artificial Sequence
<220> FEATURE:
<223> OTHER INFORMATION: Synthetic BspH1 endonuclease cleaving site in
      pUC19

<400> SEQUENCE: 6 tcatga                                                                  6

<210> SEQ ID NO 7
<211> LENGTH: 6
<212> TYPE: DNA
<213> ORGANISM: Artificial Sequence
<220> FEATURE:
<223> OTHER INFORMATION: Mutated synthetic BspH1 endonuclease cleaving
      site in pUC19

<400> SEQUENCE: 7 gcatga                                                                  6

<210> SEQ ID NO 8
<211> LENGTH: 6
<212> TYPE: DNA
```

```
<213> ORGANISM: Artificial Sequence
<220> FEATURE:
<223> OTHER INFORMATION: Synthetic Acl1 endonuclease cleave cite in
      pUC19

<400> SEQUENCE: 8 aacgtt                                                                        6

<210> SEQ ID NO 9
<211> LENGTH: 6
<212> TYPE: DNA
<213> ORGANISM: Artificial Sequence
<220> FEATURE:
<223> OTHER INFORMATION: Mutated synthetic Acl1 endonuclease cleave cite
      in pUC19

<400> SEQUENCE: 9 aacgct                                                                        6

<210> SEQ ID NO 10
<211> LENGTH: 6
<212> TYPE: DNA
<213> ORGANISM: Artificial Sequence
<220> FEATURE:
<223> OTHER INFORMATION: Mutated synthetic Acl1 endonuclease cleave cite
      in pUC19

<400> SEQUENCE: 10 cacgct                                                                        6

<210> SEQ ID NO 11
<211> LENGTH: 11
<212> TYPE: DNA
<213> ORGANISM: Artificial Sequence
<220> FEATURE:
<223> OTHER INFORMATION: Synthetic Ahd1 endonuclease cleave site in
      pUC19
<220> FEATURE:
<221> NAME/KEY: misc_feature
<222> LOCATION: (4)..(8)
<223> OTHER INFORMATION: n can be nucleotide 'a', 't', 'g', or 'c'

<400> SEQUENCE: 11
gacnnnnngt c                                                                 11

<210> SEQ ID NO 12
<211> LENGTH: 11
<212> TYPE: DNA
<213> ORGANISM: Artificial Sequence
<220> FEATURE:
<223> OTHER INFORMATION: Mutated synthetic Ahd1 endonuclease cleave site
      in pUC19
<220> FEATURE:
<221> NAME/KEY: misc_feature
<222> LOCATION: (4)..(8)
<223> OTHER INFORMATION: n can be nucleotide 'a', 't', 'g', or 'c'

<400> SEQUENCE: 12
cacnnnnngt c                                                                 11

<210> SEQ ID NO 13
<211> LENGTH: 34
<212> TYPE: DNA
<213> ORGANISM: Artificial Sequence
<220> FEATURE:
<223> OTHER INFORMATION: Synthetic multi-endonuclease product

<400> SEQUENCE: 13
```

```
ccagataaca gggtaatatt accctgttat gtgg                              34

<210> SEQ ID NO 14
<211> LENGTH: 34
<212> TYPE: DNA
<213> ORGANISM: Artificial Sequence
<220> FEATURE:
<223> OTHER INFORMATION: Synthetic multi-endonuclease product

<400> SEQUENCE: 14
ggtctattgt cccattataa tgggacaata cacc                              34

<210> SEQ ID NO 15
<211> LENGTH: 14
<212> TYPE: DNA
<213> ORGANISM: Artificial Sequence
<220> FEATURE:
<223> OTHER INFORMATION: Synthetic multi-endonuclease product

<400> SEQUENCE: 15
tagggataac ccta                                                    14

<210> SEQ ID NO 16
<211> LENGTH: 14
<212> TYPE: DNA
<213> ORGANISM: Artificial Sequence
<220> FEATURE:
<223> OTHER INFORMATION: Synthetic multi-endonuclease product

<400> SEQUENCE: 16
atcccaatag ggat                                                    14
```

METHODS FOR DYNAMIC VECTOR ASSEMBLY OF DNA CLONING VECTOR PLASMIDS

BACKGROUND OF THE INVENTION

The present invention relates in general to the field of cloning vector plasmids, and in particular to methods for rapidly assembling DNA constructs or transgenes with cloning vector plasmids.

The foundation of molecular biology is recombinant DNA technology, which can here be summarized as the modification and propagation of nucleic acids for the purpose of studying the structure and function of the nucleic acids and their protein products.

Individual genes, gene regulatory regions, subsets of genes, and indeed entire chromosomes in which they are contained, are all comprised of double-stranded anti-parallel sequences of the nucleotides adenine, thymine, guanine and cytosine, identified conventionally by the initials A, T, G, and C, respectively. These DNA sequences, as well as cDNA sequences, which are double stranded DNA copies derived from mRNA (messenger RNA) molecules, can be cleaved into distinct fragments, isolated, and inserted into a vector such as a bacterial plasmid to study the gene products. A plasmid is an extra-chromosomal piece of DNA that was originally derived from bacteria, and can be manipulated and reintroduced into a host bacterium for the purpose of study or production of a gene product. The DNA of a plasmid is similar to all chromosomal DNA, in that it is composed of the same A, T, G, and C nucleotides encoding genes and gene regulatory regions, however, it is a relatively small molecule comprised of less than approximately 30,000 base-pairs, or 30 kilobases (kb). In addition, the nucleotide base pairs of a double-stranded plasmid form a continuous circular molecule, also distinguishing plasmid DNA from that of chromosomal DNA.

Plasmids enhance the rapid exchange of genetic material between bacterial organisms and allow rapid adaptation to changes in environment, such as temperature, food supply, or other challenges. Any plasmid acquired must express a gene or genes that contribute to the survival of the host or else it will be destroyed or discarded by the organism, since the maintenance of unnecessary plasmids would be a wasteful use of resources. A clonal population of cells contains identical genetic material, including any plasmids it might harbor. Use of a cloning vector plasmid with a NA insert in such a clonal population of host cells will amplify the amount of the DNA of interest available. The DNA so cloned may then be isolated and recovered for subsequent manipulation in the steps required for building a DNA construct. Thus, it can be appreciated that cloning vector plasmids are useful tools in the study of gene function, providing the ability to rapidly produce large amounts of the DNA insert of interest.

While some elements found in plasmids are naturally occurring, others have been engineered to enhance the usefulness of plasmids as DNA vectors. These include antibiotic- or chemical-resistance genes and a multiple cloning site (MCS), among others. Each of these elements has a role in the present invention, as well as in the prior art. Description of the role each element plays will highlight the limitations of the prior art and demonstrate the utility of the present invention.

A particularly useful plasmid-born gene that can be acquired by a host is one that would confer antibiotic resistance. In the daily practice of recombinant DNA technology, antibiotic resistance genes are exploited as positive or negative selection elements to preferentially enhance the culture and amplification of the desired plasmid over that of other plasmids.

In order to be maintained by a host bacterium, a plasmid must also contain a segment of sequences that direct the host to duplicate the plasmid. Sequences known as the origin of replication (ORI) element direct the host to use its cellular enzymes to make copies of the plasmid. When such a bacterium divides, the daughter cells will each retain a copy or copies of any such plasmid. Certain strains of E. coli bacteria have been derived to maximize this duplication, producing upwards of 300 copies per bacterium. In this manner, the cultivation of a desired plasmid can be enhanced.

Another essential element in any cloning vector is a location for insertion of the genetic materials of interest. This is a synthetic element that has been engineered into "wild type" plasmids, thus conferring utility as a cloning vector. Any typical commercially-available cloning vector plasmid contains at least one such region, known as a multiple cloning site (MCS). A MCS typically comprises nucleotide sequences that are cleaved by a single endonuclease enzyme, or a series of endonuclease enzymes (, each of which has a distinct recognition sequence and cleavage pattern. The so-called recognition sequences of a restriction endonuclease (RE) site encoded in the DNA molecule comprise double-stranded palindromic sequences. For some RE enzymes, as few as 4-6 nucleotides are sufficient to provide a recognition site, while some RE enzymes require a sequence of 8 or more nucleotides. The RE enzyme EcoR1, for example, recognizes the double-stranded hexanucleotide sequence: 5' G-A-A-T-T-C 3', wherein 5' indicates the end of the molecule known by convention as the "upstream" end, and 3' likewise indicates the "downstream" end. The complementary strand of the recognition sequence would be its anti-parallel strand, 3' G-A-A-T-T-C-5'. Since every endonuclease site is a double-stranded sequence of nucleotides, a recognition site of 6 nucleotides is, in fact, 6 base pairs (bp). Thus the double stranded recognition site can be represented within the larger double-stranded molecule in which it occurs as:

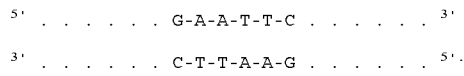

Like many other RE enzymes, EcoR1 does not cleave exactly at the axis of dyad symmetry, but at positions four nucleotides apart in the two DNA strands between the nucleotides indicated by a "/":

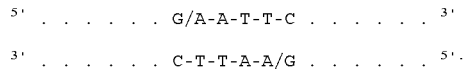

such that double-stranded DNA molecule is cleaved and has the resultant configuration of nucleotides at the newly formed "ends":

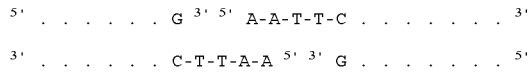

This staggered cleavage yields fragments of DNA with protruding 5' termini. Because A-T and G-C pairs are spontaneously formed when in proximity with each other, protruding ends such as these are called cohesive or sticky ends. Any one of these termini can form hydrogen bonds with any other complementary termini cleaved with the same restriction enzyme. Since any DNA that contains a specific recognition sequence will be cut in the same manner as any other DNA containing the same sequence, those cleaved ends will be complementary. Therefore, the ends of any DNA molecules cut with the same RE enzyme "match" each other in the way adjacent pieces of a jigsaw puzzle "match", and can be enzymatically linked together. It is this property that permits the formation of recombinant DNA molecules, and allows the introduction of foreign DNA fragments into bacterial plasmids, or into any other DNA molecule.

A further general principle to consider when building recombinant DNA molecules is that all endonuclease sites occurring within a molecule will be cut with a particular RE enzyme, not just the site of interest. The larger a DNA molecule, the more likely it is that any endonuclease site will reoccur. Assuming that any endonuclease sites are distributed randomly along a DNA molecule, a tetranucleotide site will occur, on the average, once every $4^4$ (i.e., 256) nucleotides or bp, whereas a hexanucleotide site will occur once every $4^6$ (i.e., 4096) nucleotides or bp, and octanucleotide sites will occur once every $4^8$ (i.e., 114,688) nucleotides or bp. Thus, it can be readily appreciated that shorter recognition sequences will occur frequently, while longer ones will occur rarely. When planning the construction of a transgene or other recombinant DNA molecule, this is a vital issue, since such a project frequently requires the assembly of several pieces of DNA of varying sizes. The larger these pieces are, the more likely that the sites one wishes to use occur in several pieces of the DNA components, making manipulation difficult at best.

Frequently-occurring endonuclease enzyme sites are herein referred to as common sites, and the endonucleases that cleave these sites are referred to as common endonuclease enzymes. Restriction enzymes with cognate restriction sites greater than 6 bp are referred to as rare restriction enzymes, and their cognate restriction sites as rare restriction sites. However, there are some endonuclease sites of 6 bp that occur more infrequently than would be statistically predicted, and these sites and the endonucleases that cleave them are also referred to as rare. Thus, the designations "rare" and common" do not refer to the relative abundance or availability of any particular restriction enzyme, but rather to the frequency of occurrence of the sequence of nucleotides that make up its cognate recognition site within any DNA molecule or isolated fragment of a DNA molecule, or any gene or its DNA sequence.

A second class of endonuclease enzymes has recently been isolated, called homing endonuclease (HE) enzymes. HE enzymes have large, non-palindromic asymmetric recognition sites (12-40 base pairs). HE recognition sites are extremely rare. For example, the HE known as I-SceI has an 18 bp recognition site, (5' . . . TAGGGATAACAGGGTAAT . . . 3'[SEQ ID NO:3]), predicted to occur only once in every $7 \times 10^{10}$ bp of random sequence. This rate of occurrence is equivalent to only one site in 20 mammalian-sized genomes. The rare nature of HE recognition sites greatly increases the likelihood that a genetic engineer can cut a final transgene product without disrupting the integrity of the transgene if HE recognition sites were included in appropriate locations in a cloning vector plasmid.

Since a DNA molecule from any source organism will be cut in identical fashion by en endonuclease enzyme, foreign pieces of DNA from any species can be cut with an endonuclease enzyme, inserted into a bacterial plasmid vector that was cleaved with the same endonuclease enzyme, and amplified in a suitable host cell. For example, if a human gene can cut in 2 places with the RE enzyme known as EcoR1, the desired fragment with EcoR1 ends can be isolated and mixed with a plasmid that was also cut with EcoR1 in what is commonly known as a ligation mixture. Under the appropriate conditions in the ligation mixture, some of the isolated human gene fragments will match up with the ends of the plasmid molecules. These newly joined ends can link together (ligated) to enzymatically recircularize the plasmid, now containing its new DNA insert. The ligation mixture is then introduced into E. coli or another suitable host, and the newly engineered plasmids will be amplified as the bacteria divide. In this manner, a relatively large number of copies of the human gene may be obtained and harvested from the bacteria. These gene copies can then be further manipulated for the purpose of research, analysis, or production of its gene product protein.

Recombinant DNA technology is frequently embodied in the generation of so-called "transgenes". Transgenes frequently comprise a variety of genetic materials that are derived from one or more donor organisms and introduced into a host organism. Typically, a transgene is constructed using a cloning vector as the starting point or "backbone" of the project, and a series of complex cloning steps are planned to assemble the final product within that vector. Elements of a transgene, comprising nucleotide sequences, include, but are not limited to 1) regulatory promoter and/or enhancer elements, 2) a gene that will be expressed as a mRNA molecule, 3) DNA elements that provide mRNA message stabilization, 4) nucleotide sequences mimicking mammalian intronic gene regions, and 5) signals for mRNA processing such as the poly-A tail added to the end of naturally-occurring mRNAs. In some cases, an experimental design may require addition of localization signal to provide for transport of the gene product to a particular subcellular location.

Each of the elements of a transgene can be derived as a fragment of a larger DNA molecule that is cut from a donor genome, or, in some cases, synthesized in a laboratory. While the present invention employs endonucleases for the methods claimed herein, it is known that each of the smaller elements comprising, for example, the inserts or modules which are used in the methods herein, can be created by de novo synthesis, recombineering, and/or PCR terminator overhang cloning. One such method of synthesis of the component elements of a transgene includes the method disclosed by Jarrell et al. in U.S. Pat. No. 6,358,712, which is incorporated herein by reference in its entirety. While Jarrell discloses a method for "welding" elements of a transgene together, only the methods of the present invention disclose a way to "unweld" and re-assemble the elements once they have been assembled. According to one aspect of the invention, each piece is assembled with the others in a precise order and 5'-3' orientation into a cloning vector plasmid.

The promoter of any gene may be isolated as a DNA fragment and placed within a synthetic molecule, such as a plasmid, to direct the expression of a desired gene, assuming that the necessary conditions for stimulation of the promoter of interest can be provided. For example, the promoter sequences of the insulin gene may be isolated, placed in a cloning vector plasmid along with a reporter gene, and used to study the conditions required for expression of the insulin gene in an appropriate cell type. Alternatively, the insulin gene promoter may be joined with the protein coding-sequence of any gene of interest in a cloning vector plasmid, and used to drive expression of the gene of interest in insulin-expressing cells, assuming that all necessary elements are present within the DNA transgene so constructed.

A reporter gene is a particularly useful component of some types of transgenes. A reporter gene comprises nucleotide sequences encoding a protein that will be expressed under the direction of a particular promoter of interest to which it is linked in a transgene, providing a measurable biochemical response of the promoter activity. A reporter gene is typically easy to detect or measure against the background of endogenous cellular proteins. Commonly used reporter genes include but are not limited to LacZ, green fluorescent protein, and luciferase, and other reporter genes, many of which are well known to those skilled in the art.

Introns, which are non-coding regions within mammalian genes, are not found in bacterial genomes, but are required for proper formation of mRNA molecules in mammalian cells. Therefore, any DNA construct for use in mammalian systems must have at least one intron. Introns may be isolated from any mammalian gene and inserted into a DNA construct, along with the appropriate splicing signals that allow mammalian cells to excise the intron and splice the remaining mRNA ends together.

An mRNA stabilization element is a sequence of DNA that is recognized by binding proteins that protect some mRNAs from degradation. Inclusion of an mRNA stabilization element will frequently enhance the level of gene expression from that mRNA in some mammalian cell types, and so can be useful in some DNA constructs or transgenes. An mRNA stabilization element can be isolated from naturally occurring DNA or RNA, or synthetically produced for inclusion in a DNA construct.

A localization signal is a sequence of DNA that encodes a protein signal for subcellular routing of a protein of interest. For example, a nuclear localization signal will direct a protein to the nucleus; a plasma membrane localization signal will direct it to the plasma membrane, etc. Thus, a localization signal may be incorporated into a DNA construct to promote the translocation of its protein product to the desired subcellular location.

A tag sequence may be encoded in a DNA construct so that the protein product will have a unique region attached. This unique region serves as a protein tag that can distinguish it from its endogenous counterpart. Alternatively, it can serve as an identifier that may be detected by a wide variety of techniques well known in the art, including, but not limited to, RT-PCR, immunohistochemistry, or in situ hybridization.

With a complex transgene, or with one that includes particularly large regions of DNA, there is an increased likelihood that there will be multiple endonuclease recognition sites in these pieces of DNA. Recall that the recognition sequences encoding any one hexanucleotide site occur every 4096 bp ($4^6$). If a promoter sequence is 3000 bp and a gene of interest of 1500 bp are to be assembled into a cloning vector of 3000 bp, it is statistically very likely that many sites of 6 or less nucleotides will not be useful, since any usable sites must occur in only two of the pieces. Furthermore, the sites must occur in the appropriate areas of the appropriate molecules that are to be assembled. In addition, most cloning projects will need to have additional DNA elements added, thereby increasing the complexity of the growing molecule and the likelihood of inopportune repetition of any particular restriction site. Since any restriction enzyme will cut at all of its sites in a molecule, if an endonuclease enzyme restriction site reoccurs, all the inopportune sites will be cut along with the desired sites, disrupting the integrity of the molecule. Thus, each cloning step must be carefully planned so as not to disrupt the growing molecule by cutting it with an endonuclease enzyme that has already been used to incorporate a preceding element. And finally, when a researcher wishes to introduce a completed transgene into a mammalian organism, the fully-assembled transgene construct frequently must be linearized at a unique recognition site at at least one end of the transgene, thus requiring yet another unique recognition site found nowhere else in the construct. Since most DNA constructs are designed for a single purpose, little thought is given to any future modifications that might need to be made, further increasing the difficulty for future experimental changes.

Traditionally, transgene design and construction consumes significant amounts of time and energy for several reasons, including the following:

1. There is a wide variety of endonuclease enzymes available that will generate an array of termini, however most of these are not compatible with each other. Many endonuclease enzymes: such as EcoR1, generate DNA fragments with protruding 5' cohesive termini or "tails"; others (e.g., Pst1) generate fragments with 3' protruding tails, whereas still others (e.g., Bal1) cleave at the axis of symmetry to produce blunt-ended fragments. Some of these will be compatible with the termini formed by cleavage with other endonuclease enzymes, but the majority of useful ones will not. The termini that can be generated with each DNA fragment isolation must be carefully considered in designing a DNA construct.

2. DNA fragments needed for assembly of a DNA construct or transgene must first be isolated from their source genomes, placed into plasmid cloning vectors, and amplified to obtain useful quantities. The step can be performed using any number of commercially-available or individually altered cloning vectors. Each of the different commercially available cloning vector plasmids were, for the most part, developed independently, and thus contain different sequences and endonuclease sites for the DNA fragments of genes or genetic elements of interest. Genes must therefore be individually tailored to adapt to each of these vectors as needed for any given set of experiments. The same DNA fragments frequently will need to be altered further for subsequent experiments or cloning into other combinations for new DNA constructs or transgenes. Since each DNA construct or transgene is custom made for a particular application with no thought or knowledge of how it will be used next, it frequently must be "retro-fitted" for subsequent applications.

3. In addition, the DNA sequence of any given gene or genetic element varies and can contain internal endonuclease sites that make it incompatible with currently available vectors, thereby complicating manipulation. This is especially true when assembling several DNA fragments into a single DNA construct or transgene.

Thus, there remains a need for a system that would allow the user to rapidly assemble a number of DNA fragments into one molecule, despite redundancy of endonuclease sites found at the ends and within the DNA fragments. Such a system might also provide a simple means for rapidly altering the ends of the fragments so that other endonuclease sequences are added to them. Inclusion of single or opposing pairs of HE sites would enhance the likelihood of having unique sites for cloning. A system that would also allow easy substitutions or removal of one or more of the fragments would add a level of versatility not currently available to users. Therefore, a "modular" system, i.e. a system allowing one to insert or remove DNA fragments or "inserts" into or out of "cassette" regions flanked by rare endonuclease sites within the cloning vector, would be especially useful and welcome to the field of recombinant DNA technology.

SUMMARY OF THE INVENTION

Accordingly, the present invention provides a method of rapidly assembling DNA constructs or transgenes by using cloning vector plasmids. The invention also provides a method that incorporates multiple DNA fragments, also known as both "inserts" or "modules", such as one each of a Promoter, Expression, and 3' Regulatory nucleotide sequence, into a cloning vector plasmid in a single step, rather than having to introduce each insert in a sequential manner. Such a method is called "Dynamic Vector Assembly" herein.

In one embodiment, the present invention provides a method for constructing a transgene, comprising the steps of providing a cloning vector plasmid with a backbone able to accept a sequential arrangement of inserts, providing at least a first insert and a second insert to be included in the transgene, and transferring both the first insert and the second insert into the backbone in a single reaction.

In another embodiment, the invention provides a method for making a transgene, comprising the steps of: providing a cloning vector plasmid comprising first and second docking points: introducing first nucleotide sequences to be included in the transgene into a first shuttle vector; introducing second nucleotide sequences to be included in the transgene into a second shuttle vector; and transferring simultaneously the first nucleotide sequences and the second nucleotide sequences from the shuttle vectors to the cloning vector plasmid, between the first and second docking points.

The invention also provides a method for making a transgene, comprising the steps of: providing a cloning vector plasmid comprising first and second docking points; introducing Promoter nucleotide sequences to be included in the transgene into a Promoter shuttle vector; introducing Expression nucleotide sequences to be included in the transgene into an Expression shuttle vector; introducing Regulatory nucleotide sequences to be included in the transgene into a Regulatory shuttle vector; and transferring simultaneously the Promoter, Expression and Regulatory nucleotide sequences from the Promoter, Expression and Regulatory shuttle vectors to the cloning vector plasmid, between the first and second docking points.

In another embodiment, the invention provides a method for simultaneously synthesizing an array of transgenes, comprising the steps of: providing a primary cloning vector plasmid comprising a first and a second docking point; introducing at least one Promoter nucleotide sequence to be included in the transgene into a corresponding Promoter shuttle vector; introducing at least one Expression nucleotide sequence to be included in the transgene into a corresponding Expression shuttle vector; introducing at least one Regulatory nucleotide sequence to be included in the transgene into a corresponding Regulatory shuttle vector; and transferring simultaneously the Promoter, Expression and Regulatory nucleotide sequences from the Promoter, Expression and Regulatory shuttle vectors to the cloning vector plasmid, between the first and second docking points, wherein at least two combinations of one Promoter module, one Expression module, and one Regulatory module are transferred into two distinct primary cloning vector molecules.

In yet another embodiment, the invention provides a method for making a modular cloning vector plasmid for the synthesis of a transgene or other complicated DNA construct, the method comprising the steps of: providing the cloning vector plasmid comprising a backbone, the backbone comprising first and second docking points, each docking point being fixed within the backbone and comprising at least one non-variable rare endonuclease site for an endonuclease enzyme; cleaving the first docking point with a first endonuclease enzyme corresponding to the at least one non-variable rare restriction site of the first docking point, leaving the cleaved first docking point with a 3' end; cleaving the second docking point with a second nuclease enzyme corresponding to the at least one non-variable rare endonuclease site of the second docking point, leaving the cleaved second docking point with a 5' end; providing at least a first and a second insert, each insert comprising a 5' end, a nucleotide sequence of interest and a 3' end, wherein the 5' end of the first insert is compatible to the 3' end of the cleaved first docking point, the 3' end of the second insert is compatible to the 5' end of the cleaved second docking point, the 3' end of the first insert being compatible to the 5' end of the second insert to form a third non-variable rare endonuclease site for a third endonuclease enzyme; and placing the inserts and the cleaved cloning vector plasmid into an appropriate reaction mixture to cause simultaneous ligation and self-orientation of the first and second inserts between the first and second docking points within the backbone, re-forming the first and second docking points, and forming the modular cloning vector plasmid.

In another embodiment, the invention provides a method for synthesizing a transgene or other complicated DNA construct, comprising the steps of: providing a primary cloning vector plasmid comprising a backbone, the backbone comprising at least a first docking point and a second docking point, each docking point being fixed within the backbone and comprising at least one rare restriction site for a non-variable rare restriction enzyme; cleaving, the first docking point with a first non-variable rare restriction enzyme corresponding to one of the rare restriction sites of the first docking point, leaving the cleaved backbone with a 3' end; cleaving the second docking point with a second non-variable rare restriction enzyme corresponding to one of the restriction sites of the second docking point, leaving the cleaved backbone with a 5' end, providing a Promoter insert into which a Promoter sequence of interest, a 5' end that is compatible to the 3' end of the first docking point, and a 3' end; providing an Expression insert comprising an Expression sequence of interest, a 5' end that is compatible to the 3' end of the Promoter insert to form a rare restriction site for a third non-variable rare restriction enzyme, and a 3' end; providing a Regulatory insert comprising a Regulatory sequence of interest, a 5' end that is compatible to the 3' end of the Expression insert to form a rare restriction site for a fourth non-variable rare restriction enzyme, and a 3' end that is compatible to the 5' end of the cleaved second docking point which was cleaved in step 'c'; and placing the Promoter, Expression and Regulatory inserts and the cleaved cloning vector plasmid into an appropriate reaction mixture to cause simultaneous ligation, self-orientation and sequential placement of the Promoter, Expression and Regulatory inserts between the first and second docking points, reforming the first and second docking points, and forming a modular primary cloning vector plasmid.

In yet another embodiment, the invention provides a method for simultaneously synthesizing an array of transgenes or other complicated DNA constructs, comprising the steps of: providing at least one primary cloning vector plasmid comprising a backbone into which inserts having a 5' end, a nucleotide sequence of interest and a 3' end can be inserted, the backbone operable to accept a sequential arrangement of Promoter, Expression, and Regulatory inserts and comprising at least a first and a second docking point, each docking point being fixed within the backbone and comprising at least one restriction site for a non-variable rare restriction enzyme; cleaving the first docking point with a first non-variable rare restriction enzyme corresponding to one of the restriction sites of the first docking point; cleaving the second docking point with a second non-variable rare restriction enzyme corresponding to one of the restriction sites of the second docking point; providing at least one Promoter insert into which a Promoter nucleotide sequence has been inserted, the 5' end of the at least one Promoter insert compatible to the 3' end of the first docking point which was cleaved in step 'b'; providing at least one Expression insert into which an Expression nucleotide sequence has been inserted, the 5' end of the at least one Expression insert being compatible to the 3' end of the at least one Promoter insert to form a restriction site for a third non-variable rare restriction enzyme; providing at least one Regulatory insert into which a Regulatory nucleotide sequence has been inserted, the 5' end of the at least one Regulatory insert being compatible to the 3' end of the at least one Expression insert to form a restriction site for a fourth non-variable rare restriction enzyme, the 3' end of the at least one Regulatory insert compatible to the 5' end of the of the second docking point which was cleaved in step 'c'; and thereafter placing at least two different types of at least one of the Promoter, Expression and Regulatory inserts, at least one of each of the remaining inserts, and the cleaved cloning vector plasmid into an appropriate reaction mixture to cause simultaneous ligation, self-orientation and sequential placement of one each of the Promoter, Expression and Regulatory inserts between the first and second docking points within the backbone, thereby creating an array of plasmids having different combinations of Promoter, Expression and Regulatory inserts within their backbone.

A further understanding of the nature and advantages of the present invention will be more fully appreciated with respect to the following drawings and detailed description.

BRIEF DESCRIPTION OF THE DRAWINGS

The accompanying drawings, which are incorporated in and constitute a part of this specification, illustrate embodiments of the invention and, together with a general description of the Invention given above, and the detailed description given below, serve to explain the principles of the invention.

DETAILED DESCRIPTION OF THE INVENTION

Figure 1:
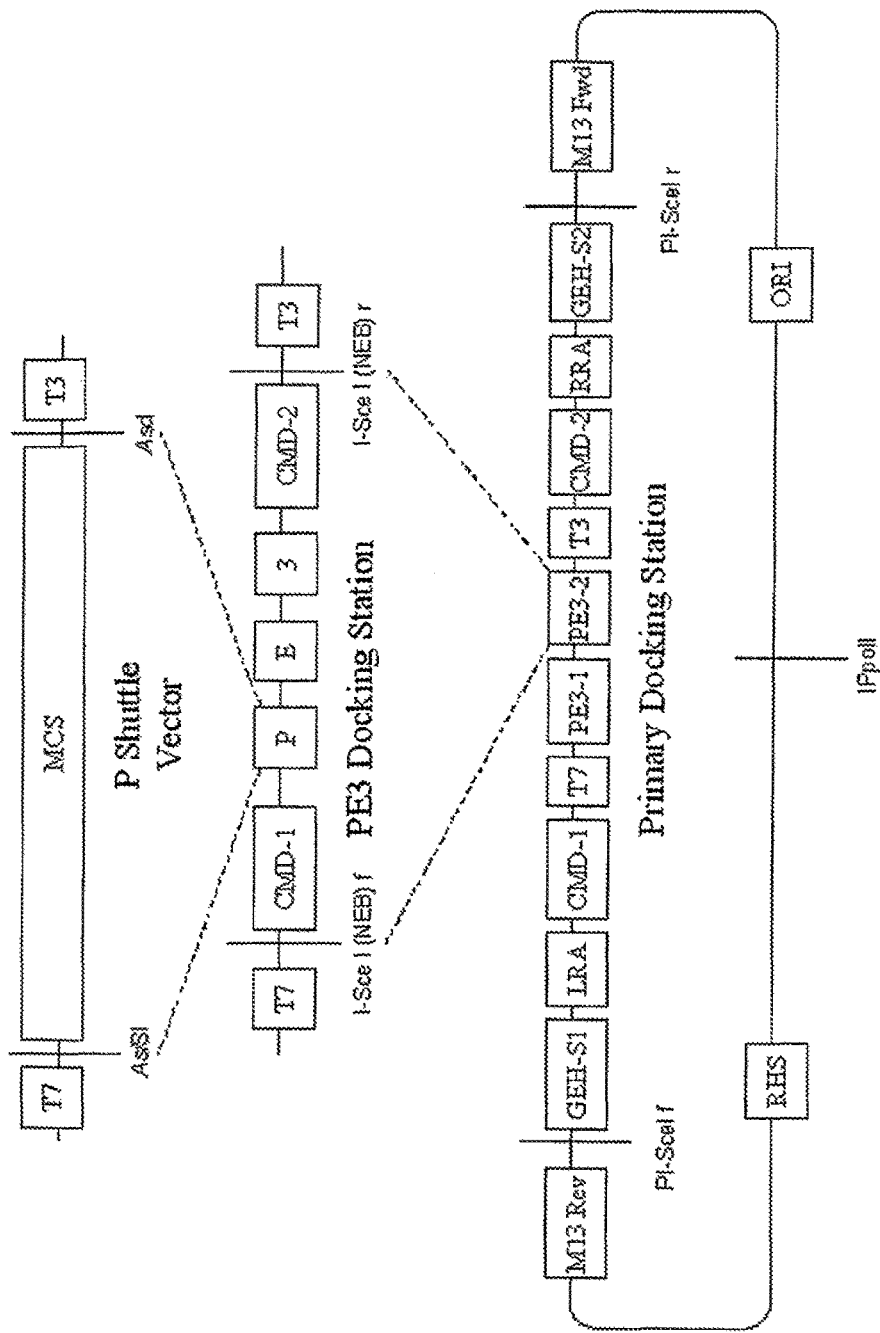
FIG. 1 is a linear map of the module concept of the invention showing a P Shuttle vector that is insertable into a PE3 docking station, which is insertable into a Primary docking station.

As used herein, the term "chromatin modification domain" (CMD) refers to nucleotide sequences that interact with a variety of proteins associated with maintaining and/or altering chromatin structure.

As used herein, the term "cloning" refers to the process of ligating a DNA molecule into a plasmid and transferring it an appropriate host cell for duplication during propagation of the host.

As used herein, the terms "cloning vector" and "cloning vector plasmid" are used interchangeably to refer to a circular DNA molecule minimally containing an Origin of Replication, a means for positive selection of host cells harboring the plasmid such as an antibiotic-resistance gene; and a multiple cloning site.

As used herein, the term "common" in relation to endonuclease sites refers to any endonuclease site that occurs relatively frequently within a genome.

As used herein, the phrase "compatible to" refers a terminus or end, either 5' or 3', of a strand of DNA which can form hydrogen bonds with any other complementary termini either cleaved with the same restriction enzyme or created by some other method. Since any DNA that contains a specific recognition sequence for a restriction enzyme will be cut in the same manner as any other DNA containing the same sequence, those cleaved ends will be complementary and thus compatible. Therefore, the ends of any DNA molecules cut with the same restriction enzyme "match" each other in the way adjacent pieces of a jigsaw puzzle "match", and can be enzymatically linked together. Compatible ends will form a recognition site for a particular restriction enzyme when combined together.

As used herein, the term "de novo synthesis" refers to the process of synthesizing double-stranded DNA molecules of any length by linking complementary single-stranded DNA molecules compatible overhangs that represent subsequences of the total desired DNA molecule.

As used herein, the term "DNA construct" refers to a DNA molecule synthesized by consecutive cloning steps within a cloning vector plasmid, and is commonly used to direct gene expression in any appropriate cell host such as cultured cells in vitro, or a transgenic moose in vivo. A transgene used to make such a mouse can also be referred to as a DNA construct, especially during the period of time when the transgene is being designed and synthesized.

As used herein, the term "DNA fragment" refers to any isolated molecule of DNA, including but not limited to a protein-coding sequence, reporter gene, promoter, enhancer, intron, exon, poly-A tail, multiple cloning site, nuclear localization signal, or mRNA stabilization signal, or any other naturally occurring or synthetic DNA molecule, or any portion thereof. Alternatively, a DNA fragment may be completely of synthetic origin, produced in vitro. Furthermore, a DNA fragment may comprise any combination of isolated naturally occurring and/or synthetic fragments.

As used herein, the term "Docking Plasmid" refers to a specialized cloning vector plasmid used in the invention to assemble DNA fragments into a DNA construct.

As used herein, the terms "endonuclease" or "endonuclease enzyme" refers to a member or members of a classification of catalytic molecules that bind a recognition site encoded in a DNA molecule and cleave the DNA molecule at a precise location within or near the sequence.

As used herein, the terms "endonuclease recognition site", recognition site", "cognate sequence" or "cognate sequences" refer to the minimal string of nucleotides required for a restriction enzyme to bind and cleave a DNA molecule or gene.

As used herein, the term "enhancer region" refers to a nucleotide sequence that Is not required for expression of a target gene, but will increase the level of gene expression under appropriate conditions.

As used herein, the term "gene expression host selector gene" (GEH-S) refers to a genetic element that can confer to a host organism a trait that can be selected, tracked, or detected by optical sensors, PCR amplification, biochemical assays, or by cell/organism survival assays (resistance or toxicity to cells or organisms when treated with an appropriate antibiotic or chemical).

As used herein, the terms "gene promoter" or "promoter" refer to a nucleotide sequence required for expression of a gene, or any portion of the full-length promoter.

As used herein, the terms "insert" and "module" are essentially interchangeable, with the only fine distinction being that an "insert" is inserted into the vector, and once it is inserted it is then more commonly called a "module". A module can then be removed from the vector. Also, the term Insert is commonly used for an isolated module used as an insert into a modular acceptor vector.

As used herein, the term "intron" refers to the nucleotide sequences of a non-protein-coding region within a mammalian cell gene found between two protein-coding regions or exons.

As used herein, the term "localization signal" (LOC) refers to nucleotide sequences encoding a signal for subcellular routing of a protein of interest.

As used herein, the term "multiple cloning site" (MCS) refers to nucleotide sequences comprising at least one unique endonuclease site, and, more typically, a grouping of unique endonuclease sites, for the purpose of cloning DNA fragments into a cloning vector plasmid As used herein, the term "mRNA stabilization element" refers a sequence of DNA that is recognized by binding proteins thought to protect some mRNAs from degradation.

As used herein, the term "Origin of Replication" (ORI) refers to nucleotide sequences that direct replication or duplication of a plasmid within a host cell.

As used herein, the phrase "PCR terminator over-hang cloning technology" refers to the process of amplifying genetic modules using the polymerase chain reaction in conjunction with single-stranded DNA primers with protected 5'over-hanging nucleotides that can serve as junction sites with complementary DNA over-hangs.

As used herein, the term "poly-A tail" refers to a sequence of adenine (A) nucleotides commonly found at the end of messenger RNA (mRNA) molecules. A Poly-A tail signal is incorporated into the 3' ends of DNA constructs or transgenes to facilitate expression of the gene of interest.

As used herein, the term "primer site" refers to nucleotide sequences that serve as DNA templates onto which single-stranded DNA oligonucleotides can anneal for the purpose of initiating DNA sequencing, PCR amplification, and/or RNA transcription.

As used herein, the term "pUC19" refers to a plasmid cloning vector well-known to those skilled in the art, and can be found in the NCBI Genbank database as Accession # L09137.

As used herein, the term "random nucleotide sequences" refers to any combination of nucleotide sequences that do not duplicate sequences encoding other elements specified as components of the same molecule. The number of nucleotides required in the random sequences is dependent upon the requirements of the endonuclease enzymes that flank the random sequences. Most endonucleases require a minimum of 2-4 additional random sequences to stabilize DNA binding. It is preferred that the number of random sequences would be a multiple of 3, corresponding to the number of nucleotides that make up a codon. The preferred minimum number of random sequences is therefore 6, however, fewer or more nucleotides may be used.

As used herein, the term "rare" in relation to endonuclease sites refers to an endonuclease site that occurs relatively infrequently within a genome.

As used herein, the term "recombination arm" refers to nucleotide sequences that facilitate the homologous recombination between transgenic DNA and genomic DNA. Successful recombination requires the presence of a left recombination arm (LRA) and a right recombination arm (RRA) flanking a region of transgenic DNA to be incorporated into a host genome vie homologous recombination.

As used herein, the term "recombineering" refers to the process of using random or site-selective recombinase enzymes in conjunction with DNA sequences that can be acted on by recombinase enzymes to translocate a portion of genetic material from one DNA molecule to a different DNA molecule.

As used herein, the term "reporter gene" refers to a nucleotide sequences encoding a protein useful for monitoring the activity of a particular promoter of interest.

As used herein, the term "Shuttle Vector" refers to a specialized cloning vector plasmid used in the invention to make an intermediate molecule that will modify the ends of a DNA fragment.

As used herein, the term "tag sequence" (TAG) refers to nucleotide sequences encoding a unique protein region that allows it to be detected, or in some cases, distinguished from any endogenous counterpart.

As used herein, the term "untranslated region" (UTR) refers to nucleotide sequences encompassing the non-protein-coding region of an mRNA molecule. These untranslated regions can reside at the 5' end (5' UTR) or the 3' end (3' UTR) an mRNA molecule.

The present invention provides a method to take a newly manufactured transgene containing the modules and selectively remove one or more of the module and replace it with a different insert. This process is called herein "second pass" and "multiple threading". The invention further provides a method for creating an array of different transgenes, each having a different Promoter, Expression and Regulatory insert, by incorporating multiple different Promoter, Expression and Regulatory inserts into a cloning vector plasmid in a single step. The present invention also provides a method that comprises the steps of providing cloning vector plasmids having newly introduced Promoter, Expression and Regulatory inserts combined together, removing the entire combination as a backbone vector, and inserting a multiple number of backbone vectors into a single cloning vector plasmid.

The present invention also provides a method to create a modular cloning vector plasmid for the synthesis of a transgene or other complicated DNA construct by providing a backbone having docking points therein. Each docking point represents an area in which there is preferably at least one fixed non-variable rare endonuclease site, and more preferably fixed groupings of two non-variable rare endonuclease sites, and most preferably fixed groupings of three non-variable rare endonuclease sites. A particular restriction site of each docking point is cleaved by its cognate endonuclease enzyme. This will create either a desired 5' or 3' end which is compatible with the complementary 5' or 3' end of one of the pre-constructed inserts containing a nucleotide sequence of choice, such as a Promoter, Expression or Regulator nucleotide sequence. At least two inserts, each of which have 5' and 3' ends that are compatible with the cleaved docking point of interest, can be added along with the cleaved cloning vector plasmid to an appropriate reaction mixture, and, assuming the proper thermodynamic milieu, the inserts can simultaneously, i.e. in a single step, become integrated into the cloning vector plasmid. During this singular addition and ligation reaction, the docking points are reformed and the cloning vector plasmid becomes modular, in that the docking points and the connection between the two modules can be re-cleaved with the appropriate restriction enzymes. The module can then later be removed, and a new module can be put in its place.

One embodiment of the present invention relates to a method for constructing a transgene, comprising the steps of providing a cloning vector plasmid with a backbone able to accept a sequential arrangement of inserts, providing at least a first insert and a second insert to be included in the transgene, and transferring both the first insert and the second insert to the backbone in a single reaction. More preferably the inserts consist of three inserts, specifically at least one Promoter, Expression, and Regulatory module.

Another embodiment of the invention is a method for making a transgene comprising the steps of providing a cloning vector plasmid comprising first and second docking points, introducing Promoter nucleotide sequences to be included in the transgene into a Promoter shuttle vector, introducing Expression nucleotide sequences to be included in the transgene into an Expression shuttle vector, introducing Regulatory nucleotide sequences to be included in the transgene into a Regulatory shuttle vector, transferring simultaneously the Promoter, Expression and Regulatory nucleotide sequences from the Promoter, Expression and Regulatory shuttle vector to the cloning vector plasmid, between the first and second docking points.

It is preferred that both the 5' and 3' ends of each of the docking points and each of the inserts all are compatible with a corresponding end of another docking point or insert. For example, if a first docking point contains a restriction site for a non-variable rare restriction enzyme such as SgrAI and that docking point is thereafter cleaved, then a first insert intended to be inserted at the 3' end of the cleaved first docking point will contain a compatible 5' end to create a restriction site for SgrAI when the insert is combined with the first docking point. A second docking point within the plasmid may, for example, have a restriction site for a non-variable restriction enzyme such as SwaI. Any second insert will have at its 3' end a compatible nucleotide sequence to combine with the cleaved 5' end of the cleaved second docking point to create a restriction site for SwaI. Further, the 3' end of the first insert and the 5' end of the second insert, in order to simultaneously be inserted into the modular cloning vector plasmid and also thereafter be removed at the same point, must contain compatible ends to create a third restriction site for a third non-variable rare restriction enzyme, such as PacI or SalI.

Sequential elements encoding the modular structure of the present invention can specifically comprise: three non-variable and unique common restriction sites, a 5' oligonucleotide primer site, a unique HE site in a forward orientation, a pair of non-variable and unique, common restriction sites flanking random nucleotide sequences, a fixed grouping of non-variable rare restriction sites to define a 5' portion of a promoter module, random nucleotide sequences, a fixed grouping of non-variable rare restriction sites that define a shared junction between a 3' position relative to the Promoter/intron module and a 5' position relative to an Expression module, random nucleotide sequences, a fixed grouping of non-variable rare restriction sites that define a junction of a 3' position relative to the Expression module and a 5' position relative to a 3' Regulatory module, random nucleotide sequences, a fixed grouping of non-variable rare restriction sites that define a 3' position relative to a 3' Regulatory module, a pair of non-variable and unique, common restriction sites flanking random nucleotide sequences, a unique HE site in reverse orientation that is the same HE site as that placed 3' of the 5' oligonucleotide primer site, a 3' oligonucleotide primer site in reverse orientation, and four non-variable and unique co restriction sites that define a 3' insertion site.

Other sequential elements encoding the modular structure of the present invention can specifically comprise: two non-variable and unique common restriction sites that define a 5' insertion site, an oligonucleotide primer site, a pair of unique HE sites in opposite orientation flanking random nucleotide sequences, a non-variable and unique, common restriction site that allows cloning of a shuttle vector module downstream of the pair of unique HE sites, a fixed grouping of non-variable rare restriction sites, random nucleotide sequences, a fixed grouping of non-variable rare restriction sites, a unique HE site in a forward orientation, a pair of non-variable and unique, common restriction sites flanking random nucleotide sequences, an oligonucleotide primer site, a pair of unique BstX I sites in opposite orientations (wherein the variable nucleotide region in the BstX I recognition site is defined by nucleotides identical to the non-complementary tails generated by the ordering of two identical HE recognition sites arranged in reverse-complement orientation, a pair of unique HE sites in opposite orientations flanking random nucleotide sequences; an oligonucleotide primer site in reverse-orientation, a pair of non-variable and unique, common restriction sites flanking random nucleotide sequences, a unique HE site in reverse orientation, with the HE site being the same as the HE site in a forward orientation, a fixed grouping of non-variable rare restriction sites, random nucleotide sequences, a fixed grouping of non-variable rare restriction sites, a non-variable and unique, common restriction site, a pair of unique HE sites in opposite orientation flanking random nucleotide sequences, an oligonucleotide primer site in reverse orientation, and three non-variable and unique common restriction sites.

The present invention is a group of methods for assembling a variety of DNA fragments into a de novo DNA construct or transgene by using cloning vectors optimized to reduce the amount of manipulation frequently needed.

The primary vector, herein referred to as a Docking Plasmid, contains a multiple cloning site (MCS) with preferably 3 sets of rare endonuclease sites arranged in a linear pattern. This arrangement defines a modular architecture that allows the user to assemble multiple inserts into a single transgene construct without disturbing the integrity of DNA elements already incorporated into the Docking Plasmid in previous cloning steps.

Two recognition sites for at least three HE are placed in opposite orientation to flank three modular regions for the purpose of creating a gene cassette acceptor site that cannot self-anneal. Because HE sites are asymmetric and non-palindromic, it is possible to generate non-complementary protruding 3' cohesive tails by placing two HE recognition sites in opposite orientation. Thus, the HE I-Scel cuts its cognate recognition site as Indicated by "/";

```
5'...T A G G G A T A A / C A G G G T A A T...3',

3'...A T C C C / T A T T G T C C A T T A...5'.
```

The reverse placement of a second site within an MCS would generate two non-complementary cohesive protruding tails:

```
5'...TAGGGATAA      CCCTA...3'

3'...ATCCCAATAGGGAT...5'.
```

This is particularly useful when it is necessary to subclone larger transgenes into a vector. Due to the size of the insert, it is thermodynamically more favorable for a vector to self anneal rather than accept a large insert. The presence of non-complementary tails generated by this placement of restriction sites provides chemical forces to counteract the thermodynamic inclination for self-ligation.

The asymmetric nature of most HE protruding tails also creates a powerful cloning tool when used in combination with the BstX I endonuclease enzyme site (5' CCANNNNN/NTGG 3', where 'N' can be any nucleotide [SEQ ID NO:5]). The sequence-neutral domain of BstX I can be used to generate compatible cohesive ends for two reverse-oriented HE protruding tails, while precluding self-annealing.

BstX I (I-Sce I Fwd.) I-Sce I Forward I-Sce I Reverse BstX I (I-Sce I Rev.)

```
5'-CCAGATAA  CAGGGTAAT//ATTACCCTGTTAT     GTGG-3'

3'-GGTC      TATTGTCCCATTA//TAATGGGAC AATACACC-5'
```

Endonuclease sites used in the invention were chosen according to a hierarchy of occurrence. In order to determine the frequency of endonuclease site occurrence, DNA sequence information corresponding to nineteen different genes was analyzed using Vector NTI software. This search covered a total of 110,630 nucleotides of DNA sequence. Results from these analyses were calculated according to the number of instances of an endonuclease site occurring within the analyzed 110,530 nucleotides. Endonuclease sites were then assigned a hierarchical designation according to four classifications, wherein "common" sites occur greater than 25 times per 110,530 nucleotides, "lower-frequency 6 bp sites" occur between 6-24 times per 110,530 nucleotides, and "rare" sites occur between 0-5 times per 110,530 nucleotides. A partial list of "suitable" enzymes is hereby listed according to their occurrence classifications:

Common endonuclease enzymes:
Ase I, BamH I, Bgl II, Blp I, BstX I, EcoR I, Hinc II, Hind III, Nco I, Pst I, Sac I, Sac II, Sph I, Stu I, Xba I Endonuclease enzymes that have a 6 bp recognition site, but have a lower frequency of occurrence:
Aar I, Aat H, Afl II, Age I, ApaL I, Avr II, BseA I, BspD I, BspE I, BstB I, Cia I, Eag I, Eco0109 I, EcoR V, Hpa I, Kpn I, Mfe I, Nar I, Nde I, NgoM IV, Nhe I, Nsi I, Pml I, SexA I, Sma I, Spe I, Xho I Rare endonuclease enzymes:
Acl I, Asc I, AsiS I, BsiW I, Fse I, Mlu I, Not I, Nru I, Pac I, Pme I, Pvu I, Rsr II, Sal I, Sbf I, Sfi I, SgrA I, SnaB I, Swa I, Pl-Sce I, I-Sce I, I-Ceu I, Pl-Psp I, I-Ppo I, I-Tli I Other endonucleases not included in these listings can also be used, maintaining the same functionality and the spirit and intent of the invention.

The secondary vectors of the invention, herein known as Shuttle vectors, contain multiple cloning sites with common endonuclease sites flanked by rare endonuclease sites. The shuttle vectors are designed for cloning fragments of DNA into the common endonuclease sites between the rare sites. The cloned fragments can subsequently be released by cleavage at the rare endonuclease site or sites, and incorporated into the Docking Plasmid using the same rare endo-nuclease site or sites found in the shuttle vectors.

Thus, unlike conventional cloning vectors, the design of the MCS allows "cassettes" or modules of DNA fragments to be inserted into the modular regions of the Docking Plasmid. Likewise, each can be easily removed using the same rare endonuclease enzymes, and replaced with any other DNA fragment of interest. This feature allows the user to change the direction of an experimental project quickly and easily without having to rebuild the entire DNA construct, Thus, the cloning vector plasmids of the present invention allow the user to clone a DNA fragment into an intermediate vector using common endonuclease sites, creating a cassette-accepting module, and to then transfer that fragment to the desired modular spot in the final construct by means of rare endonuclease sites. Furthermore, it allows future alterations to the molecule to replace individual modules in the Docking Plasmid with other cassette modules. The following descriptions highlight distinctions of the present invention compared with the prior art.

Individual components of a transgene (the promoter enhancer P, expressed protein E, and/or 3' regulatory region 3) can be assembled as modules transferred from shuttle vectors into the PE3 Docking Station Plasmid. If higher orders of complexity are needed, the assembled transgenes, or other nucleotide sequences, can then be transferred into a Primary Docking Plasmid. Each of the five types of cloning vector plasmids will be explained in greater detail to provide an understanding of the components incorporated into each, beginning with the more complex PE3 Docking Station Plasmid and the Primary Docking Plasmid.

The PE3 Docking Plasmid comprises a pUC19 backbone with the following modifications, wherein the sequences are numbered according to the pUC19 Genbank sequence fife, Accession # L09137:

1. Only sequences from 806 to 2617 (Afl3-Aat2) are used in the Docking Plasmid,

2. The BspH1 site at 1729 in pUC19 rs mutated from TCATGA to GCATGA,

3. The AO site at 1493 in pUC19 is mutated from AACGTT to AACGCT,

4. The Acl1 site at 1120 in pUC19 is mutated from AACGTT to CACGCT,

5. The Ahd1 site in pUC19 is mutated from GACNNNNNGTC to CACNNNNNGTC [SEQ ID NOS:11 and 12], 6. Sequences encoding BspH1/I-Ppo 1/BspH1 are inserted at the only remaining BspH1 site in pUC19 following the mutation step 2 in the list above.

The multiple cloning site (MCS) in the PE3 Docking Plasmid comprises the following sequential elements, in the order listed:

1. Three non-variable and unique common endonuclease sites that define a 5' insertion site for the mutated pUC19 vector described above (shown as, but not limited to, Aat II, Blp I, and EcoO109 I);

2. A T7 primer site;

3. A unique HE site (for example, I-SceI (forward orientation));

4. A pair of non-variable and unique, common endonuclease sites flanking random nucleotide sequences that can serve as a chromatin modification domain acceptor module (RNAS-CMD-1) (for example, Kpn I and Avr II);

5. A fixed grouping of non-variable rare endonuclease sites that define the 6' portion of the promoter module (for example, AsiS I, Pac I, and Sbf 1);

6. Random nucleotide sequences that can serve as a Promoter/intron acceptor module (RNAS-P);

7. A fixed grouping of non-variable rare endonuclease sites that define the shared junction between the 3' portion of the Promoter/intron module and the 5' portion of the Expression module (for example, SgrA I, AscI, and MluI);

8. Random nucleotide sequences that can serve as an expression acceptor module (RNAS-E);

9. A fixed grouping of non-variable rare endonuclease sites that define the junction of the 3' portion of the Expression module and the 5' portion of the 3' Regulatory module (for example, SnaB I, Not I, and Sal I);

10. Random nucleotide sequences that can serve as a regulatory domain acceptor module (RNAS-3);

11. A fixed grouping of non-variable rare endonuclease sites that define the 3' portion of the 3' Regulatory module (for example, Swa I, Rsr II, and BsiW I);

12. A pair of non-variable and unique, common endonuclease sites flanking a random nucleotide sequence of DNA that can serve as a chromatin modification domain acceptor module (RNAS-CMD-2) (for example, Xho I and Nhe I);

13. A unique HE site in reverse orientation that is identical to that in item 3, above;

14. A T3 primer site in reverse orientation; and

15. Four non-variable and unique common endonuclease sites that define a 3' insertion site for the mutated pUC19 vector described above (for example, BspE I, Pme I, Sap I, and BspH I).

The Primary Docking Plasmid can be used to assemble two completed transgenes that are first constructed in PE3 Docking Station Plasmids, or two homology arms needed to construct a gene-targeting transgene, or to introduce two types of positive or negative selection elements. The multiple cloning site (MCS) in the Primary Docking Plasmid comprises the following sequential elements, in the order listed:

1. Two non-variable and unique common endonuclease sites that define a 5' insertion site for the mutated pUC19 vector described above (for example, Aat II and Blp I);

2. An M13 Rev. primer site;

3. A pair of unique endonuclease flanking a random nucleotide sequence of DNA that can serve as a genome expression host selector gene acceptor module (RNAS-GEH-S1);

4. A non-variable and unique, common endonuclease site that allows cloning of a shuttle vector module downstream of the HE pair (for example, EcoO109I);

5. A fixed grouping of non-variable rare endonuclease sites that define the 5' portion a Left Recombination Arm module (for example, AsiS I Pac I, and Sbf I);

6. Random nucleotide sequences that can serve as a Left Recombination Arm acceptor module (RNAS-LRA);

7. A fixed grouping of non-variable rare endonuclease sites that define the 3' portion of the Left Recombination Arm acceptor module (for example, SgrA I, MluI, and AscI);

8. A unique HE site (for example, I-Ceu I (forward orientation));

9. A pair of non-variable and unique, common endonuclease sites flanking a random nucleotide sequence of DNA that can serve as a chromatin modification domain acceptor module (RNAS-CMD-1) (for example, Kpn I and Avr II);

10. A T7 primer site;

11. A pair of unique BstX I sites in opposite orientation (wherein the variable nucleotide region in the BstX I recognition site is defined by nucleotides identical to the non-complementary tails generated by the ordering of two identical HE recognition sites arranged in reverse-complement orientation; for example, PI-SceI (forward orientation) and PI-SceI (reverse orientation)) flanking a random nucleotide sequence of DNA that can serve as a complex transgene acceptor module (RNAS-PE3-1);

12. A pair of unique endonuclease sites flanking a random nucleotide sequence of DNA that can serve as a complex transgene acceptor module (RNAS-PE3-2);

13. A T3 primer site in reverse-orientation;

14. A pair of non-variable and unique, common endonuclease sites flanking a random nucleotide sequence of DNA that can serve as a chromatin modification domain acceptor module (RNAS-CMD-2) (for example, Xho I and Nhe I);

15. A unique HE site in reverse orientation that is identical to that in item 8 above;

16. A fixed grouping of non-variable rare endonuclease sites that define the 5' portion a Right Recombination Arm module (for example, SnaB I, Sal and Not I);

17. Random nucleotide sequences that can serve as a Right Recombination Arm acceptor module (RNAS-RRA);

18. A fixed grouping of non-variable rare endonuclease sites that define the 3' portion of the Right Recombination Arm acceptor module (for example, Rsr II, Swa I, and BsiW I);

19. A non-variable and unique, common endonuclease site that allows cloning of a shuttle vector module (for example, BspE I);

20. A pair of unique endonuclease sites flanking a random nucleotide sequence of DNA that can serve as a genome expression host selector gene acceptor module (RNAS-GEH-S2);

21. An M13 Forward primer site placed in reverse orientation; and

22. Three non-variable and unique common endonuclease sites that define a 3' insertion site for the mutated pUC19 vector described above (for example, Pme I, Sap I, and BspH I).

Three cloning vector plasmids of the invention are known as Shuttle Vectors. The Shuttle Vectors, like the PE3 and Primary Docking Plasmids, are also constructed from a pUC19 backbone. Just like the PE3 and Primary Docking Plasmids, each Shuttle Vector has the same modifications to the pUC19 backbone listed as 1 through 6, above. The individual Shuttle Vectors (SV) are identified as Shuttle Vector Promoter/intron (P), Shuttle Vector Expression (E), and Shuttle Vector 3'Regulatory (3); henceforth SVP, SVE, and SV3, respectively. Each is described more fully below.

Shuttle Vector P (SVP):

SVP is a cloning vector plasmid that can be used to prepare promoter and intron sequences for assembly into a transgene construct. An example of an SVP Plasmid can comprise the following sequential elements in the MCS, in the order listed:

1. Two non-variable and unique, common endonuclease sites that define a 5' insertion site for the mutated pUC19 vector described above (for example, AatII and BlpI);

2. A T7 primer site;

3. A non-variable and unique, common endonuclease site that allows efficient cloning of a shuttle vector module downstream of the T7 primer site (for example, Eco0109I);

4. A fixed grouping of non-variable rare endonuclease sites that define the 5' portion of the promoter module (for example, AsiSI, Pac I, and Sbf I), These non-variable rare endonuclease sites provide the docking point represented by the star at the 5' end of the Promoter Vector of FIG. 2;

5. A variable MCS comprising any grouping of common or rare endonuclease sites that are unique to the shuttle vector;

6. A fixed grouping of non-variable rare endonuclease sites that define the 3' portion of the promoter module (for example, SgrA I, AscI, and MluI). These non-variable rare endonuclease sites provide the docking point represented by the circle at the 3' end of the Promoter Vector of FIG. 2;

7. A non-variable and unique, common endonuclease site that allows efficient cloning of a shuttle vector module upstream of the T3 primer site (for example, BspEI);

8. A reverse-orientation T3 primer site; and

9. Two non-variable and unique, common endonuclease sites that define a 3' insertion site for the mutated pUC19 vector described above (for example, PmeI and SapI).

Shuttle Vector E (SVE):

This is a cloning vector plasmid that can be used to prepare sequences to be expressed by the transgene for assembly into a transgene construct. An example of an SVE plasmid can comprise the following sequential elements in the MCS, in the order listed:

1. Two non-variable and unique, common endonuclease sites that define a 5' insertion site for the mutated pUC19 vector described above (for example, AatII and Blp \I);

2. A T7 primer site;

3. A non-variable and unique, common endonuclease site that allows efficient cloning of a shuttle vector module downstream of the T7 primer site (for example, Eco0109\I);

4. A fixed grouping of non-variable rare endonuclease sites that define the 5' portion of the expression module (for example, SgrA I, AscI, and MluI). These non-variable rare endonuclease sites provide the docking point represented by the circle at the 5' end of the Expression Vector of FIG. 2;

5. A variable MCS consisting of any grouping of common or rare endonuclease sites that are unique to the shuttle vector;

6. A fixed grouping of non-variable rare endonuclease sites that define the 3' portion of the expression module (for example, SnaBI, NotI, and SalI). These non-variable rare endonuclease sites provide the docking point represented by the triangle at the 3' end of the Expression Vector of FIG. 2;

7. A non-variable and unique, common endonuclease site that allows efficient cloning of a shuttle vector module upstream of the T3 primer site (for example, BspEI);

8. A reverse-orientation T3 primer site; and

9. Two non-variable and unique, common restriction sites that define a 3' insertion site for the mutated pUC19 vector described above (for example, PmeI and SapI).

Shuttle Vector 3 (SV3):

This is a cloning vector plasmid that can be used to prepare 3' regulatory sequences for assembly into a transgene construct. An example of an SV3 plasmid can comprise the following elements in the MCS, in the order listed:

1, Two non-variable and unique, common endonuclease sites that define a 5' insertion site for the mutated pUC19 vector described above (for example, AatII and BlpI);

2. A T7 primer site;

3. A non-variable and unique, common endonuclease site that allows efficient cloning of a shuttle vector module downstream of the T7 primer (for example, Eco0109I);

4. A fixed grouping of non-variable rare endonuclease sites that define the 5' portion of the 3' regulatory module (for example, SnaBI, NotI, and SalI), These non-variable rare endonuclease sites provide the docking point represented by the triangle at the 5' end of the Regulatory Vector of FIG. 2.

5. A variable MCS consisting of any grouping of common or rare endonuclease sites that are unique to the shuttle vector;

6. A fixed grouping of non-variable rare endonuclease sites that define the 3' portion of the 3' regulatory module (for example, SwaI, RsrII, and BsiWI). These non-variable rare endonuclease sites provide the docking point represented by the square at the 3' end of the Regulatory Vector of FIG. 2;

7. A non-variable and unique, non-rare endonuclease site that allows efficient cloning of a shuttle vector module upstream of the 13 primer site (for example, BspEI);

8. A reverse-orientation T3 primer site; and

9. Two non-variable and unique, non-rare endonuclease sites that define a 3' insertion site for the mutated pUC19 vector described above (for example, PmeI and SapI).

While the present invention discloses methods for building transgenes in plasmid cloning vectors, similar methods can be used to build transgenes in larger extrachromosomal DNA molecules such as cosmids or artificial chromosomes, including bacterial artificial chromosomes (BAC). For use in plants, a T1 vector may also be used. The wide variety of genetic elements that can be incorporated into the plasmid cloning vectors also allow transfer of the final transgene products into a wide variety of host organisms with little or no further manipulation.

Figure 2:
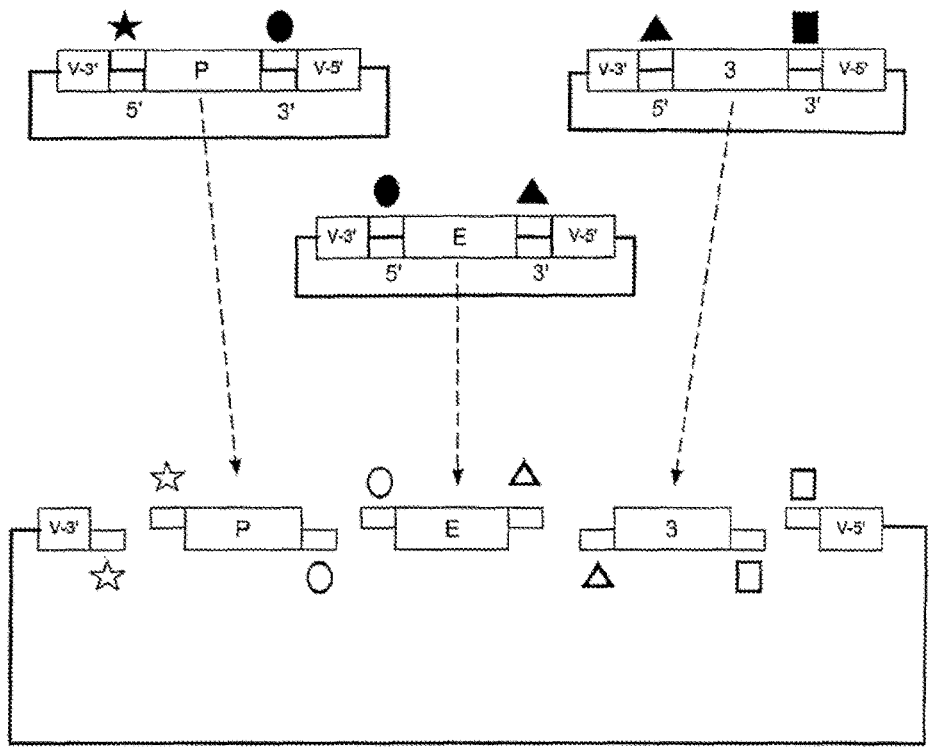
FIG. 2 is an illustration depicting assembly of a backbone vector enabled by the relationships between restriction sites within shuttle vectors such as Promoter, Expression and 3 Regulatory modules, and the docking points on a primary cloning vector plasmid.
Figure 3:
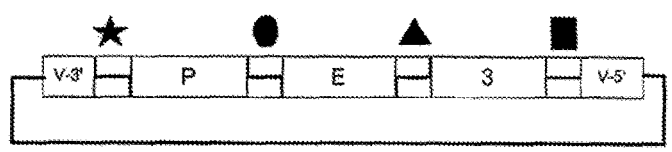
FIG. 3 is an illustration depicting assembled backbone vector of FIG. 2.

FIGS. 2 and 3 are a general illustration of the modularity of the invention. As shown in FIG. 2, there is one each of a Promoter, Expression, and 3' Regulatory shuttle vector. Flanking each insert within the shuttle vectors are endonuclease restriction sites that are specific for creating a docking point. More specifically, in FIG. 2, the Promoter insert (P) is flanked by a first group of one or more endonuclease restriction sites represented by aster at the 5' end and a second group of one or more endonuclease restriction sites represented by a circle at the 3' end; the Expression module is flanked by the second group of endonuclease restriction sites represented by the circle at the 5' end and a third group of one or more endonuclease restriction sites represented by a triangle at the 3' end; and the 3' Regulatory module (3) is flanked by the third group of endonuclease restriction sites represented by the triangle at the 5' end and a fourth group of one or more endonuclease restriction sites represented by a square at the 3' end. Cleaving each endonuclease recognition site by the endonuclease specific for that site creates sticky ends at the 5' and 3' end of each module, as indicated in bottom portion of FIG. 2 by the inserts at the end of the dashed line arrows. The modules can now be combined with a cloning vector plasmid which has also been cleaved at its two fixed docking points by endonucleases specific for the first group of endonuclease restriction sites (represented by the star) and the fourth group of endonuclease restriction sites (represented by the square). When the modular vectors are placed with the cloning vector plasmid in an appropriate reaction mixture, the cleaved sticky ends (represented by hollow stars, circles, triangles and squares) of each modular vector will self-orient within the plasmid and sequentially ligate, with the cleaved star ends combining, the cleaved circle ends combining, the cleaved triangle ends combining, and the cleaved square ends combining. This results in an assembled backbone vector shown in FIG. 3. Further, each of the combined groups of endonuclease sites represented by the star, circle, triangle, and square can once again be cleaved by its corresponding specific endonuclease, such that a particular insert can later be removed and replaced with another insert of interest.

Multiple backbone vectors (example, PE3-1 and PE3-2) can be inserted into a single docking plasmid. The asymmetric nature of the protruding tails of an endonuclease such as I-Sce I, as with other HE's, creates a powerful cloning tool when used in combination with the BstX I endonuclease enzyme site (5' CCANNNNN/NTGG 3', where 'N' can be any nucleotide [SEQ ID NO:5]). The sequence-neutral domain of BstX I can be used to generate compatible cohesive ends for two reverse-oriented I-Sce I protruding tails, while precluding self-annealing. With this method, a first insert, PE3-1, having an I-Sce-1 site at its ends can be placed in a cloning vector plasmid by cleaving the plasmid at the Bstx1/Sca1 endonuclease sites. One can then cut again with I-SceI and insert a PE3-2 having I-Sce-1 site at its ends. This entire backbone can then be cleaved from its docking plasmid by PI-Sce I and inserted into another docking plasmid that contains BstX I/PI-Sce I endonuclease sites. This second docking plasmid also has endonuclease sites for PI-Sce I, into which yet another module for a separate docking plasmid, possible containing a PE3-3 and PE3-4, can be inserted (not shown). In this manner, a researcher can get more information into one cell, that is, one can insert multiple genes within the context of a single vector, which has not previously been accomplished by those skilled in the art. Such a novel process can save a both money and time for researchers working in this field.

EXAMPLES

Example 1

PE3 Docking Plasmid

As an example of the method of practicing the present invention, a transgene can be constructed containing these elements:
1. Nucleotide sequences of the human promoter for surfactant protein C (SP-C);
2. Sequences encoding the protein product of the mouse gene granulocyte-macrophage colony-stimulating factor-receptor beta c (GMRβc);
3. Rabbit betaglobin intron sequences; and
4. SV40 poly-A signal.

The SP-C sequences contain internal BamH1 sites, and can be released from its parental plasmid only with Not1 and EcoR1. GMRβc has an internal Not 1 site, and can be cut from its parental plasmid with BamH1 and Xho1. The rabbit betaglobin intron sequences can be cut out of its parental plasmid with EcoR1. The SV40 poly-A tail can be cut from its parental plasmid with Xho1 and Sac1. Because of redundancy of several of endonuclease sites, none of the parental plasmids can be used to assemble all the needed fragments.

The steps used to build the desired transgene in the PE3 Docking Plasmid invention are as follows.

1. Since Not1 and PspOM1 generate compatible cohesive ends, the human SP-C promoter sequences are excised with Not1 and EcoR1 and cloned into the PspOM1 and EcoR1 sites of Shuttle Vector P. The product of this reaction is called pSVP-SPC 2. Following piopagation and recovery steps well known to those skilled in the art, the rabbit betaglobin intron sequences are cloned into the EcoR1 site of pSVP-SPC. Orientation of the intron in the resultant intermediate construct is verified by sequencing the product, called pSVP-SPC-rG.

3. The promoter and intron are excised and isolated as one contiguous fragment from pSVP-SPC-rβG using AsiS1 and Asc1. Concurrently, the PE3 Docking Plasmid is cut with AsiS1 and Asc1 in preparation for ligation with the promoter/intron segment. The promoter/intron fragment is ligated into the Docking Plasmid, propagated, and recovered.

4. The Xho1 site of the GMRβc fragment is filled in to create a blunt 3' end, using techniques well known to those skilled in the art. It is then cloned into the BamH1 site and the blunt-ended Pvu2 site of pSVP-SPC-rβG. The resultant plasmid (pDP-SPC-GMRβc-rβG) was propagated and recovered.

5. The final cloning step is the addition of the SV-40 Poly-A tail. The SV40-polyA fragment is cut out with Xho1 and Sac1, as is the recipient vector pDS1-SPC-GMRβc-rbβG. Both pieces of DNA are gel purified and recovered. A ligation mix is prepared with a 10:1 molar ratio of SV-40polyA to pDS1-SPC-GMRβc-rβG. The ligation products are propagated and harvested. The new plasmid, pDS1-SPC-GMRββc-rβG-pA contains all elements required for the transgene, including a unique endonuclease site at the 3' end with which the entire pDS1-SPC-GMRβc-rβG-pA plasmid can be linearized for transfection into eukaryotic cells or microinjection into the pronucleus of a fertilized ovum.

Example 2

Dynamic Vector Assembly

Dynamic Vector Assembly is illustrated in the following example:

1. Promoter sequences from the human cytomegalovirus (CMV) are inserted into a P Shuttle Vector (SVP), having AsiSI and Ase I endonuclease at the 5' and 3' portions, respectively. Plasmids are amplified, and the promoter module is cleaved from the vector by AsiS I and Asc I endonuclease digestion and isolated.

2. Sequences encoding a luciferase protein are inserted into an Expression Shuttle Vector (SVE), having Asc I and Not 1 endonuclease at the 5' and 3' portions, respectively. Plasmids are amplified, and the Expression module is cleaved from the vector by Asc I and Not 1 endonuclease digestion and isolated.

3. Sequences encoding a mammalian intron and SV40 poly-adenylation site are inserted into a 3' Regulatory Shuttle vector (SVS), having Not I and BsiW I endonuclease at the 5' and 3' portions, respectively. Plasmids are amplified, and the Regulatory module is cleaved from the vector by Not 1 and BsiW I endonuclease digestion and isolated.

4. The endonuclease recognition sites in a Docking Vector plasmid having AsiS I and BsiW I endonuclease at the 5' portion of the promoter module and the 3' portion of the regulator module, respectively, are cleaved with AsiS I and BsiW I endonuclease and isolated.

5. The Promoter, Expression, and Regulatory modules are combined with the Docking Vector Plasmid in a ligation mixture. Following an incubation of 2 hours, the ligation mixture is used to transform E. coli, which are then spread on an LB agar plate with ampicillin. The plate is incubated at 37° C. overnight. Colonies are isolated and propagated in individual liquid LB broth cultures. The plasmid DNA is isolated from each LB broth culture. The DNA is analyzed by endonuclease mapping to determine whether the plasmids from each colony contain the three modular inserts (Promoter, Expression and Regulatory). A plasmid that contains the three modular inserts is identified as the transgene pCMV-luc-SV40 pA. It can be linearized using I-Sce I endonuclease and injected into mouse pronuclei to generate CMV-luciferase mice. The CMV promoter in this example directs the expression of the luciferase gene in ail tissues of a host organism, such as a CMV-luciferase mouse.

Example 3

Redesign of a Dynamic Vector Assembly

If the researcher now wishes to refine the expression pattern so that luciferase is expressed only in a particular tissue or cell-type, he or she can quickly and easily replace the CMV promoter with one that will provide a restricted expression pattern. The following example Illustrates the use of the invention to facilitate rapid redesign of pCMV-luc-pA:

1. A neuron-specific promoter, Neuron-Specific Enolase (NSE), is inserted into a P Shuttle Vector (SVP) and prepared as the Promoter Module in the previous example.

2. pCMV-luc-pA is cleaved with AsiS I and Asc I to remove the CMV Promoter Module. The remainder of the Docking Vector Plasmid containing intact Expression and Regulatory Modules is isolated.

3. The NSE Promoter Module is placed in a ligation mixture with the remainder of the Docking Vector Plasmid containing intact Expression and Regulatory Modules. Following incubation for 2 hours, the new ligation mixture is used to transform E. coli. The E. coli mixture is spread on an LB agar plate with ampicillin, as in the previous example. Colonies are isolated the following day, propagated, and plasmid DNA is isolated from each. Endonuclease mapping is used to identify plasmids that contain the desired NSE Promoter module.

Example 4

Array of Transgenes

The following example is an illustration of the use of the invention to rapidly assemble an array of transgenes, each containing a different combination of Promoter, Expression, and Regulatory modules. A series of six shuttle vectors and a PE3 docking station vector will be used to generate eight different vector products using combinatorial assembly. The series of six shuttle vectors consists of two P-Shuttles (SVP), two E-Shuttles (SVE), and two 3-Shuttles (SV3). The two discrete P-Shuttles (SVP) contain either a human cytomegalovirus (CMV) promoter or a mouse SPC lung-specific promoter, and each has AsiS I and Asc I endonuclease at the 5' and 3' portions, respectively. The two discrete E-Shuttles contain either a Luciferase cDNA or an EGFP cDNA and each has Asc I and Not 1 endonuclease at the 5' and 3' portions, respectively. The two discrete 3-Shuttle vectors contain either an SV40 polyA signal or the 3' regulatory region of the human growth hormone (hGH) and each has Not I and BsiW I endonuclease at the 5' and 3' portions, respectively.

The promoter modules are released from their respective SVP shuttle vectors by individually digesting appropriate shuttle vector with the AsiS I and the Asc I endonucleases. The resulting restriction products are individually subjected to gel electrophoresis and the DNA band corresponding to the appropriate promoter module is subjected to gel purification. This procedure will yield either a CMV promoter module or an SPC promoter module bounded on the 5' side by an AsiS I overhang and by an Asc I overhang on the 3' end.

The expression modules are released from their respective SVE shuttle vectors by individually digesting appropriate shuttle vector with the Asc I and the Not I restriction endonucleases. The resulting restriction products are individually subjected to gel electrophoresis and the DNA band corresponding to the appropriate expression module is subjected to gel purification. This procedure will yield either a Luciferase expression module or an EGFP expression module bounded on the 5' side by an Asc I overhang and by a Not I overhang on the 3' end.

The 3' regulatory modules are released from their respective SV3 shuttle vectors by individually digesting appropriate shuttle vector with the Not I and the BsiW I restriction endonucleases. The resulting restriction products are individually subjected to gel electrophoresis and the DNA band corresponding to the appropriate 3' regulatory module is subjected to gel purification. This procedure will yield either a SV40 3' regulatory module or an hGH 3' regulatory module bounded on the 5' side by a Not 1 overhang and by a BsiW I overhang on the 3' end.

The PE3 docking station vector is prepared by digesting with the AsiS I and the BsiW I restriction endonucleases. To help prevent future vector re-ligation, the vector restriction digest is exposed to calf intestinal phosphatase (CR) for one hour at 37° C. The resulting CIP-treated vector restriction product is then subjected to gel electrophoresis and the DNA band corresponding to linearized PE3 vector backbone is subjected to gel purification.

Samples from the seven resulting gel-purified DNA fragments are analyzed for identity, integrity, purity, and quantity by running out on a diagnostic electrophoretic gel. Quantitative data concerning the relative abundance of the purified PE3 docking station vector and the respective DNA modules is used to define the amount of each component needed for a combinatorial ligation reaction.

When setting up a ligation reaction, there are two strategies that frequently lead to successful results. The first strategy is to set up ligation reaction mixtures wherein the insert-to-vector ratio is about 3:1. The second strategy, used when more than one insert is being introduced to a single vector simultaneously, is to introduce a molar equivalent of each genetic module that will be inserted into the vector. This can be achieved either by adding a variable volume of the modules to a reaction container in order to obtain molar equivalence in the context of the ligation reaction mixture, or by adding a neutral buffer solution to each of the purified modules so that their concentrations are equivalent on a molar ratio basis. In this example, the gel-purified vector and insert fragments have all been adjusted to molar equivalence using the buffer 10 mM Tris, pH 8.0. The total ligation reaction volume is set at 150 microliters. The ligation reaction mixture consists of the following constituents: 39 microliters of uitrapure water, 15 microliters of 10× Ligase buffer, 5 microliters of the purified PE3 vector backbone, 15 microliters of the purified CMV Promoter module, 15 microliters of the purified SPC Promoter module, 15 microliters of the purified Luciferase expression module, 15 microliters of the purified EGFP expression module, 15 microliters of the purified SV40 3' regulatory module, 15 microliters of the purified hGH 3' regulatory module, and 1 microliter of ligase enzyme. The resulting reaction components are thoroughly mixed and then incubated overnight at 16° C.

The predicted vector ligation products include the following:

pCMV-EGFP-SV40
pCMV-EGFP-hGH
pCMV-Luciferase-SV40
pCMV-Luciferase-hGH
pSPC-EGFP-SV40
pSPC-EGFP-hGH
pSPC-Luciferase-SV40
pSPC-Luciferase-hGH The ligation mixture is then used to transform *E. coli*, which are then spread on an LB agar plate with ampicillin. The plate is incubated at 37° C. overnight. Colonies are isolated and propagated in individual liquid LB broth cultures. The plasmid DNA is isolated from each LB broth culture. The DNA is analyzed by endonuclease mapping to determine the identity of the resulting vector incorporated into each colony.

In the preceding example, one of the predicted vector products (pCMV-EGFP-SV40) was not produced during the first combinatorial process. One vector that was successfully produced (pCMV-Luciferase-SV40) can, however, serve as a vector backbone for producing the desired pCMV-EGFP-SV40 vector. This technique can be referred to as "Second Pass Assembly".

Example 5

Second Pass Assembly

In order to build the desired pCMV-EGFP-SV40 vector, the pCMV-Luciferase-SV40 vector product of Example 4 is digested with Asc I and Not I, CI P-treated, and subsequently gel-purified. This linearized vector fragment, in which the Luciferase module has been removed, is incubated in a ligation mixture containing the EGFP module produced in the previous example of combinatorial vector assembly.

The ligation mixture is used to transform *E. coli*, which are then spread on an LB agar plate with ampicillin. The plate is incubated at 37° C. overnight. Colonies are isolated and propagated in individual liquid LB broth cultures. The plasmid DNA is isolated from each LB broth culture. The DNA is analyzed by endonuclease mapping to determine whether the plasmids from each colony contain the EGFP insert.

Among the many advantages of the present invention, it can readily be appreciated that one can rapidly assemble an array of transgenes, each containing a different combination of Promoter, Expression, and Regulatory modules, in a very short period of time, as well as quickly and easily vary or redesign a newly assemble transgene. In the past, varying an assembled transgene using known methods to create an array of different transgenes, each having different Promoter, Expression, and Regulatory modules would usually take a year or more of laboratory time. Using the methods of the present invention, one can make the same number of desired transgenes within days or weeks, and then do the desired testing of each, thereby saving the researcher a previously large amount of time. Further, both Dynamic Vector Assembly, in which one each of a Promoter, Expression and Regulatory insert can be inserted into a single backbone at the same time, and the combination method described, in which two P-Shuttles, two E-Shuttles, and two Regulatory-Shuttles are all combined to create eight different types of transgenes, can be used to save precious time and money for researchers. Shuttles that were originally created by de novo synthesis, recombineering, and PCR terminator over-hang cloning methods can be taken and used with the docking point technology of the present invention to rapidly assemble these pre-made elements into a multitude of transgenes.

While the present invention has been illustrated by the description of embodiments thereof, and while the embodiments have been described in detail, it is not intended to restrict or in any way limit the scope of the appended claims to such detail. Additional advantages and modifications will be readily apparent to those skilled in the art. The invention in its broader aspects is therefore not limited to the specific details, representative methods and structures, and illustrated examples shown and described. Accordingly, departures may be made from such details without departing from the scope or spirit of Applicant's general inventive concept.

What is claimed is:

1. A method for making a transgene, comprising:
   (a) providing a cloning vector plasmid comprising first and second docking points, wherein each docking point comprises at least one endonuclease site of greater than six nucleotides, wherein the cloning vector plasmid further comprises a unique homing endonuclease site in a forward orientation located upstream from the 5' end of the first docking point and a unique homing endonuclease site in a reverse orientation located downstream from the 3' end of the second docking point;
   (b) introducing a first nucleotide sequence into a first shuttle vector;
   (c) introducing a second nucleotide sequence into a second shuttle vector; and
   (d) transferring simultaneously the first nucleotide sequence and the second nucleotide sequence from the shuttle vectors to the cloning vector plasmid, between the first and second docking points.

2. A method for making a transgene, comprising:
   (a) providing a cloning vector plasmid comprising first and second docking points, wherein each docking point comprises at least one endonuclease site of greater than six nucleotides, wherein the cloning vector plasmid further comprises a unique homing endonuclease site in a forward orientation located upstream from the 5' end of the first docking point and a unique homing endonuclease site in a reverse orientation located downstream from the 3' end of the second docking point;
   (b) introducing a Promoter nucleotide sequence into a Promoter shuttle vector;
   (c) introducing an Expression nucleotide sequence into an Expression shuttle vector;
   (d) introducing a Regulatory nucleotide sequence into a Regulatory shuttle vector; and
   (e) transferring simultaneously the Promoter, Expression and Regulatory nucleotide sequences from the Promoter, Expression and Regulatory shuttle vectors into the cloning vector plasmid, between the first and second docking points.

3. A method for making a modular cloning vector plasmid for the synthesis of a transgene or other DNA construct, the method comprising:
   (a) providing cloning vector plasmid comprising a backbone, the backbone comprising first and second docking points, each docking point being fixed within the backbone and comprising at least one endonuclease site of greater than six nucleotides, wherein the cloning vector plasmid further comprises a unique homing endonuclease site in a forward orientation located upstream from the 5' end of the first docking point and a unique homing endonuclease site in a reverse orientation located downstream from the 3' end of the second docking point;
   (b) cleaving the first docking point with a first endonuclease enzyme corresponding to the at least one endonuclease site of greater than six nucleotides of the first docking point, leaving the cleaved first docking point with a 3' end;
   (c) cleaving the second docking point with a second nuclease enzyme corresponding to the at least one endonuclease site of greater than six nucleotides of the second docking point, leaving the cleaved second docking point with a 5' end;
   (d) providing at least a first and a second insert, each insert comprising a 5' end, a nucleotide sequence of interest and a 3' end, wherein the 5' end of the first insert is compatible with the 3' end of the cleaved first docking point, the 3' end of the second insert is compatible with the 5' end of the cleaved second docking point, the 3' end of the first insert being compatible with the 5' end of the second insert to form a third endonuclease site of greater than six nucleotides for a third endonuclease enzyme; and (e) placing the inserts and the cleaved cloning vector plasmid into an appropriate reaction mixture to cause simultaneous ligation and self-orientation of the first and second inserts between the first and second docking points within the backbone, thereby re-forming the first and second docking points, thereby forming the modular cloning vector plasmid.

4. The method of claim 3, further comprising:

(f) subsequently removing the first insert by cleaving the modular cloning vector plasmid at the first docking point and the third endonuclease site of greater than six nucleotides with the first and the third endonuclease enzymes, leaving a 3' end at the cleaved first docking point and a 5' end at the cleaved third endonuclease site;

(g) providing a third insert comprising a 5' end, a nucleotide sequence of interest and a 3' end, wherein the 5' end of the third insert is compatible with the 3' end of the cleaved first docking point, and the 3' end of the third insert is compatible with the 5' end of the cleaved third endonuclease site; and (h) placing the third insert and the cleaved modular cloning vector plasmid into an appropriate reaction mixture to cause simultaneous ligation and self-orientation of the third insert between the first docking point and the third endonuclease site, thereby re-forming the first docking point and the third endonuclease site.

5. The method of claim 3, further comprising:

(i) subsequently removing the second insert by cleaving the modular cloning vector plasmid at the first docking point and the third endonuclease site of greater than six nucleotides with the second and the third endonuclease enzymes, leaving a 3' end at the cleaved third endonuclease site and a 5' end at the cleaved docking point;

(j) providing a fourth insert comprising a 5' end, a nucleotide sequence of interest and a 3' end, wherein the 5' end of the fourth insert is compatible with the 3' end of the cleaved third endonuclease site, and the 3' end of the fourth insert is compatible with the 5' end of the cleaved second docking point; and (k) placing the fourth insert and the cleaved modular cloning vector plasmid into an appropriate reaction mixture to cause simultaneous ligation and self-orientation of the fourth insert between the third endonuclease site and the second docking point, thereby re-forming the third endonuclease site and the second docking point.

6. The method of claim 3, wherein the inserts are created by a method selected from the group consisting of de novo synthesis, recombineering, and PCR terminator over-hang cloning.

7. A method for synthesizing a transgene or other DNA construct, comprising:

(a) providing a primary cloning vector plasmid comprising a backbone, the backbone comprising at least a first docking point and a second docking point, each docking point being fixed within the backbone and comprising at least one endonuclease site of at least six nucleotides for a non-variable restriction enzyme, wherein the cloning vector plasmid further comprises a unique homing endonuclease site in a forward orientation located upstream from the 5' end of the first docking point and a unique homing endonuclease site in a reverse orientation located downstream from the 3' end of the second docking point;

(b) cleaving the first docking point with a first non-variable rare restriction enzyme corresponding to one of the endonuclease sites of greater than six nucleotides of the first docking point, leaving the cleaved backbone with a 3' end;

(c) cleaving the second docking point with a second non-variable rare restriction enzyme corresponding to one of the endonuclease sites of greater than six nucleotides of the second docking point, leaving the cleaved backbone with a 5' end;

(d) providing a Promoter insert into which a Promoter sequence of interest, a 5' end that is compatible with the 3' end of the first docking point, and a 3' end;

(e) providing an Expression insert comprising an Expression sequence of interest, a 5' end that is compatible with the 3' end of the Promoter insert to form a endonuclease site of greater than six nucleotides for a third non-variable rare restriction enzyme, and a 3' end;

(f) providing a Regulatory insert comprising a Regulatory sequence of interest, a 5' end that is compatible with the 3' end of the Expression insert to form a endonuclease site of greater than six nucleotides for a fourth non-variable rare restriction enzyme, and a 3' end that is compatible with the 5' end of the cleaved second docking point; and (g) placing the Promoter, Expression and Regulatory inserts and the cleaved cloning vector plasmid into an appropriate reaction mixture to cause simultaneous ligation, self-orientation and sequential placement of the Promoter, Expression and Regulatory inserts between the first and second docking points, reforming the first and second docking points, and forming a modular primary cloning vector plasmid.

8. The method of claim 7, further comprising:

(h) cleaving the modular primary cloning vector plasmid with a pair of rare restriction enzymes at a corresponding pair of endonuclease sites of greater than six nucleotides of at least one of the Promoter, Expression and Regulatory inserts, leaving the cleaved vector plasmid with a 3' end and a 5' end;

(i) providing at least one fifth insert selected from a Promoter insert, an Expression insert, and a Regulatory insert, the fifth insert having a 5' end that is compatible with the 3' end of the cleaved vector plasmid, and a 3' end that is compatible with the 5' end of the cleaved vector plasmid; and (j) placing the fifth insert and the cleaved vector plasmid into an appropriate reaction mixture to cause simultaneous ligation and self-orientation of the fifth insert into the modular primary cloning vector plasmid, in the same sequence, thereby re-forming the pair of endonuclease sites of greater than six nucleotides.

9. The method of claim 8, further comprising repeating said cleaving, providing and placing for one or more additional inserts selected from a Promoter insert, an Expression insert, and a Regulatory insert.

10. A method for simultaneously synthesizing an array of transgenes or other DNA constructs, comprising:

(a) providing at least one primary cloning vector plasmid comprising a backbone into which inserts having a 5' end, a nucleotide sequence of interest and a 3' end can be inserted, the backbone operable to accept a sequential arrangement of Promoter, Expression, and Regulatory inserts and comprising at least a first and a second docking point, each docking point being fixed within the backbone and comprising at least one endonuclease site of greater than six nucleotides for a non-variable rare restriction enzyme, wherein the cloning vector plasmid further comprises a unique homing endonuclease site in a forward orientation located upstream from the 5' end of the first docking point and a unique homing endonuclease site in a reverse orientation located downstream from the 3' end of the second docking point;

(b) cleaving the first docking point with a first non-variable rare restriction enzyme corresponding to one of the endonuclease sites of greater than six nucleotides of the first docking point;

(c) cleaving the second docking point with a second non-variable rare restriction enzyme corresponding to one of the endonuclease sites of greater than six nucleotides of the second docking point;

(d) providing at least one Promoter insert into which a Promoter nucleotide sequence has been inserted, the 5' end of the at least one Promoter insert compatible with the 3' end of the cleaved first docking point (e) providing at least one Expression insert into which an Expression nucleotide sequence has been inserted, the 5' end of the at least one Expression insert being compatible with the 3' end of the at least one Promoter insert to form a an endonuclease site of greater than six nucleotides for a third non-variable rare restriction enzyme;

(f) providing at least one Regulatory insert into which a Regulatory nucleotide sequence has been inserted, the 5' end of the at least one Regulatory insert being compatible with the 3' end of the at least one Expression insert to form endonuclease site of greater than six nucleotides for a fourth non-variable rare restriction enzyme, the 3' end of the at least one Regulatory insert being compatible with the 5' end of the of the cleaved second docking point; and (g) placing at least two different types of at least one of the Promoter, Expression and Regulatory inserts, at least one of each of the remaining inserts, and the cleaved cloning vector plasmid into an appropriate reaction mixture to cause simultaneous ligation, self-orientation and sequential placement of one each of the Promoter, Expression and Regulatory inserts between the first and second docking points within the backbone, thereby creating an array of plasmids having different combinations of Promoter, Expression and Regulatory inserts within their backbone.

11. The method of claim 10, wherein said placing comprises placing at least two different types of at least two of the Promoter, Expression and Regulatory inserts, at least one of each of the remaining inserts, and the cleaved cloning vector plasmid into an appropriate reaction mixture to cause simultaneous ligation, self-orientation and sequential placement of one each of the Promoter, Expression, and Regulatory inserts between the first and second docking points within the backbone, thereby creating an array of plasmids having different combinations of Promoter, Expression and Regulatory inserts within their backbone.

12. The method of claim 10, wherein said placing comprises placing at least two different types of each of the Promoter, Expression and Regulatory inserts and the cleaved cloning vector plasmid into an appropriate reaction mixture to cause simultaneous ligation, self-orientation and sequential placement of one each of the Promoter, Expression, and Regulatory inserts between the first and second docking points within the backbone, thereby creating an array of plasmids having different combinations of Promoter, Expression and Regulatory inserts within their backbone.

13. The method of claim 10, further comprising:
(h) assaying the products of said placing using high throughput screening;
i. isolating a specific product of said placing which is a primary cloning vector plasmid;
(j) cleaving the backbone of the isolated primary cloning vector plasmid at the 5' and 3' ends of one of the Promoter, Expression and Regulatory inserts with the pair of rare restriction enzymes corresponding thereto;
(k) providing a sixth insert, wherein the 5' end of the sixth insert is compatible with the 3' end of the cleaved backbone, wherein the 3' end of the sixth insert is compatible with the 5' end of the cleaved backbone; and
(l) placing the sixth insert and the cleaved backbone into an appropriate reaction mixture to cause simultaneous ligation and self-orientation of the sixth insert into the backbone.

14. The method of claim 13, further comprising repeating said assaying, isolating, cleaving, providing and placing to sequentially replace one insert for another insert into the backbone.

15. The method of claim 10, wherein the inserts are created by a method selected from the group consisting of de novo synthesis, recombineering, PCR, terminator over-hang cloning technology, and restriction endonuclease mapping.

16. The method of any of claims claim 3, the method further comprising:
(m) cleaving the backbone at each of the unique homing endonuclease sites with a unique homing endonuclease restriction enzyme;
(n) purifying the cleaved portion containing the inserts; and
(o) inserting the cleaved portion into a genome host of interest.

17. A method of preparing one or more transgenes comprising:
(a) providing a cloning vector plasmid comprising at least a first and a second docking point, wherein said first and said second docking points each comprise a nucleotide sequence that is recognized by at least a first and a second rare restriction enzyme, respectively, and wherein said first and said second rare restriction enzyme are different from each other, and wherein the cloning vector plasmid further comprises a unique homing endonuclease site in a forward orientation located upstream from the 5' end of the first docking point and a unique homing endonuclease site in a reverse orientation located downstream from the 3' end of the second docking point;
(b) digesting said cloning vector plasmid using said first and said second rare restriction enzyme to obtain a digested vector having a 5' end and a 3' end;
(c) providing at least a first and a second polynucleotide insert wherein each of said first and second polynucleotide inserts comprises a 5' insert end, a nucleotide sequence of interest and a 3' insert end;
(d) placing said first polynucleotide insert and said second polynucleotide insert and said digested vector together into an appropriate reaction mixture to allow simultaneous annealing and ligating of said inserts and said digested vector, thereby obtaining an insert-bearing vector, wherein said first polynucleotide insert and said second polynucleotide insert and said digested vector anneal and ligate with each other in a predetermined order and orientation such that said first docking point of said cloning vector is re-formed between said 5' end of said first polynucleotide insert and said 3' end of said digested vector, and said second docking point of said cloning vector is re-formed between said 3' insert end of said second insert and said 5' end of said digested vector, wherein at least one additional docking point is formed between the re-formed first and re-formed second docking points, and wherein each additional docking point comprises a nucleotide sequence that is recognized by an additional rare restriction enzyme that is different from said first rare and said second rare restriction enzymes.

18. The method of claim 17, wherein said at least first and second polynucleotide inserts are prepared by a method selected from the group consisting of de novo synthesis, recombineering, and PCR.

19. The method of claim 17 wherein said additional docking point is formed between the re-formed first and second docking points upon ligation of said 3' end of said first polynucleotide insert and said 5' end of said second polynucleotide insert.

20. The method of claim 17, wherein said first polynucleotide insert comprises a promoter sequence and said second polynucleotide insert comprises a nucleotide sequence selected from the group consisting of an enhancer sequence, a promoter sequence, a gene of interest, a gene capable of being expressed as an mRNA,. an expression module, an intron, a reporter sequence, a tag sequence, a splicing signal sequence, an RNA stabilization element, and a regulatory sequence.

21. The method of claim 17, further comprising providing a third polynucleotide insert, wherein a third docking point and a fourth docking point are formed between the re-formed first and re-formed second docking points upon ligation of said first polynucleotide insert, said second polynucleotide insert, said third polynucleotide insert, and said digested vector.

22. The method of claim 21, wherein said first polynucleotide insert comprises a promoter sequence, said second polynucleotide insert comprises an expression module sequence, and said third polynucleotide insert comprises a regulatory sequence, respectively.

23. The method of claim 21, further comprising providing a fourth polynucleotide insert, wherein a fifth docking point and a sixth docking point are formed between the re-formed first and re-formed second docking points upon ligation of said first polynucleotide insert, said second polynucleotide insert, said third polynucleotide insert, said fourth polynucleotide insert, and said digested vector.

24. The method of claim 17, wherein said first and second docking points each comprise a nucleotide sequence that is recognized by more than one rare restriction enzyme.

25. The method of claim 17 further comprising:
(e) digesting said insert-bearing vector to remove at least one polynucleotide insert from said insert-bearing vector thereby providing a digested insert-bearing vector;
(f) placing at least one different polynucleotide insert(s) and said digested insert-bearing vector into a reaction vessel under appropriate conditions to allow annealing and ligation of nucleic acids, wherein said different polynucleotide insert(s) and said digested vector anneal and ligate with each other in a predetermined order and orientation such that said first docking point of said cloning vector is again re-formed and at least one additional docking point is formed between the re-formed first docking point and the re-formed second docking point, and wherein said additional docking point(s) comprises a nucleotide sequence that is recognized by an additional rare restriction enzyme that is different from said first and said second rare restriction enzymes.

26. The method of claim 25, wherein the insert that is removed is a first promoter and said different insert is a second promoter.

27. The method of claim 17 further comprising:
(e) digesting said insert-bearing vector to remove at least one polynucleotide insert from said insert-bearing vector thereby providing a digested insert-bearing vector;
(f) placing at least one different polynucleotide insert(s) and said digested insert-bearing vector into a reaction vessel under appropriate conditions to allow annealing and ligation of nucleic acids, wherein said different polynucleotide insert(s) and said digested vector anneal and ligate with each other in a predetermined order and orientation such that said second docking point of said cloning vector is again re-formed and at least one additional docking point is formed between the re-formed first docking point and the re-formed second docking point, and wherein said additional docking point(s) comprises a nucleotide sequence that is recognized by an additional rare restriction enzyme that is different from said first and said second rare restriction enzymes.

28. The method of claim 27, wherein the insert that is removed is a first expression module and said different polynucleotide insert is a second expression module.

29. The method of claim 17, wherein each of said first rare restriction enzyme and said second rare restriction enzyme is selected from the group consisting of Acl I, Asc I, AsiS I, BsiW I, Fse I, Mlu I, Not I, Nm I, Pac I, Pme I, Pvu I, Rsr II, Sal I, Sbf I, Sfi I, SgrA I, SnaB I, Swa I, Pl-Sce I, I-Sce I, I-Ceu I, PL-Psp I, I-Ppo I, and I-Tli I.

30. The method of claim 25, wherein the additional rare restriction enzyme is selected from the group consisting of Acl I, Asc I, AsiS I, BsiW I, Fse I, Mlu I, Not I, Nm I, Pac I, Pme I, Pvu I, Rsr II, Sal I, Sbf I, Sfi I, SgrA I, SnaB I, Swa I, Pl-Sce I, I-Sce I, I-Ceu I, PL-Psp I, I-Ppo I, and I-Tli I.

31. The method of claim 27, wherein the additional rare restriction enzyme is selected from the group consisting of Acl I, Asc I, AsiS I, BsiW I, Fse I, Mlu I, Not I, Nm I, Pac I, Pme I, Pvu I, Rsr II, Sal I, Sbf I, Sfi I, SgrA I, SnaB I, Swa I, Pl-Sce I, I-Sce I, I-Ceu I, PL-Psp I, I-Ppo I, and I-Tli I.

32. The method of claim 7, the method further comprising:
(m) cleaving the backbone at each of the unique homing endonuclease sites with a unique homing endonuclease restriction enzyme;
(n) purifying the cleaved portion containing the inserts; and
(o) inserting the cleaved portion into a genome host of interest.

33. The method of claim 10, the method further comprising:
- (m) cleaving the backbone at each of the unique homing endonuclease sites with a unique homing endonuclease restriction enzyme;
- (n) purifying the cleaved portion containing the inserts; and
- (o) inserting the cleaved portion into a genome host of interest.

* * * * *